(12) United States Patent
Lee et al.

(10) Patent No.: US 10,625,043 B2
(45) Date of Patent: Apr. 21, 2020

(54) ELECTRONIC APPARATUS AND METHOD FOR MANAGING SLEEP

(71) Applicant: Samsung Electronics Co., Ltd., Suwon-si, Gyeonggi-do (KR)

(72) Inventors: Keumkoo Lee, Yongin-si (KR); Joayoung Lee, Bucheon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 639 days.

(21) Appl. No.: 15/372,945

(22) Filed: Dec. 8, 2016

(65) Prior Publication Data

US 2017/0173299 A1 Jun. 22, 2017

(30) Foreign Application Priority Data

Dec. 21, 2015 (KR) ........................ 10-2015-0182945

(51) Int. Cl.
*A61M 21/02* (2006.01)
*A61M 11/08* (2006.01)
(Continued)

(52) U.S. Cl.
CPC .......... *A61M 21/02* (2013.01); *A61B 5/0077* (2013.01); *A61B 5/024* (2013.01); *A61B 5/11* (2013.01);
(Continued)

(58) Field of Classification Search
CPC ................. A61M 21/02; A61M 11/08; A61M 2205/3303; A61M 2021/0077; A61M 16/0069; A61M 16/1055; A61M 16/101; A61M 2230/63; A61M 2205/52; A61M 2205/505; A61M 2205/3592; A61M 2205/3569; A61M 2205/3561; A61M 2205/3553; A61M 2205/3365; A61M 2230/40; A61M 2230/06; A61B 5/4806; A61B 5/4839; A61B 5/4812; A61B 5/4815; A61B 2560/0242; A61B 5/024;
(Continued)

(56) References Cited

U.S. PATENT DOCUMENTS 4,523,589 A * 6/1985 Krauser ................ A61M 15/00
128/203.27
6,397,845 B1 * 6/2002 Burton ................ A61M 16/024
128/204.23
(Continued)

FOREIGN PATENT DOCUMENTS

KR 10-2007-0099880 A 10/2007

*Primary Examiner* — Jenna Zhang
(74) *Attorney, Agent, or Firm* — Jefferson IP Law, LLP

(57) ABSTRACT

An electronic device is provided. The electronic device includes a capsule container configured to contain at least one capsule, a discharge structure configured to discharge a material included in the capsule, a transceiver configured to transmit data to an external device or to receive data from the external device, and at least one processor. The at least one processor is configured to receive, user state information and biometric information from the external device via the transceiver, select at least one capsule in the capsule container on the basis of the received user state information and biometric information, determine a spray amount of a material contained in the selected at least one capsule, and spray the material via the discharge structure.

20 Claims, 22 Drawing Sheets

(51) Int. Cl.
*A61M 16/00* (2006.01)
*A61B 5/00* (2006.01)
*A61M 16/10* (2006.01)
*A61B 5/16* (2006.01)
*A61B 5/11* (2006.01)
*A61B 5/113* (2006.01)
*A61B 5/024* (2006.01)
*A61M 21/00* (2006.01)

(52) U.S. Cl.
CPC ............ *A61B 5/113* (2013.01); *A61B 5/1118* (2013.01); *A61B 5/165* (2013.01); *A61B 5/4812* (2013.01); *A61B 5/4839* (2013.01); *A61B 5/4866* (2013.01); *A61B 5/6891* (2013.01); *A61M 11/08* (2013.01); *A61M 16/0069* (2014.02); *A61M 16/101* (2014.02); *A61M 16/1055* (2013.01); A61M 2560/0242 (2013.01); A61M 2021/0077 (2013.01); A61M 2205/3303 (2013.01); A61M 2205/3365 (2013.01); A61M 2205/3553 (2013.01); A61M 2205/3561 (2013.01); A61M 2205/3569 (2013.01); A61M 2205/3592 (2013.01); A61M 2205/505 (2013.01); A61M 2205/52 (2013.01); A61M 2230/06 (2013.01); A61M 2230/40 (2013.01); A61M 2230/63 (2013.01)

(58) Field of Classification Search
CPC ......... A61B 5/6891; A61B 5/113; A61B 5/11; A61B 5/4866; A61B 5/1118; A61B 5/165; A61B 5/0077
See application file for complete search history.

(56) References Cited

U.S. PATENT DOCUMENTS

| | | | |
|---|---|---|---|
| 7,463,142 B2* | 12/2008 | Lindsay | A61B 5/00 340/539.12 |
| 7,953,613 B2* | 5/2011 | Gizewski | G06F 19/3456 705/3 |
| 2006/0175426 A1 | 8/2006 | Schramm et al. | |
| 2007/0023044 A1* | 2/2007 | Kwok | A61M 16/0057 128/204.23 |
| 2007/0173705 A1* | 7/2007 | Teller | A61B 5/02055 600/300 |
| 2008/0011292 A1* | 1/2008 | Sugita | A61M 5/16827 128/200.19 |
| 2012/0041778 A1 | 2/2012 | Kraft | |
| 2012/0179012 A1* | 7/2012 | Saffarian | A61B 5/0022 600/324 |
| 2014/0188286 A1 | 7/2014 | Hunka | |
| 2014/0206964 A1 | 7/2014 | Saffarian | |
| 2014/0290646 A1* | 10/2014 | Koehler | A61M 16/06 128/200.14 |
| 2016/0217672 A1* | 7/2016 | Yoon | A61B 5/4812 |
| 2017/0095670 A1* | 4/2017 | Ghaffari | A61B 5/0024 |
| 2017/0181474 A1* | 6/2017 | Cameron | A24F 47/008 |
| 2017/0231560 A1* | 8/2017 | Hyde | A61B 5/7495 340/870.07 |
| 2018/0110960 A1* | 4/2018 | Youngblood | A61B 5/0031 |
| 2018/0207393 A1* | 7/2018 | Baek | H05B 47/105 |
| 2019/0021641 A1* | 1/2019 | Feuerstein | A61B 5/165 |

* cited by examiner

ELECTRONIC APPARATUS AND METHOD FOR MANAGING SLEEP

CROSS-REFERENCE TO RELATED APPLICATION(S)

This application claims the benefit under 35 U.S.C. § 119(a) of a Korean patent application filed on Dec. 21, 2015 in the Korean Intellectual Property Office and assigned Serial number 10-2015-0182945, the entire disclosure of which is hereby incorporated by reference.

TECHNICAL FIELD

The present disclosure relates to an electronic apparatus and a sleep management method. More particularly, the present disclosure relates to an electronic apparatus for acquiring user's sleep information to induce a sleep, and a method of managing the sleep.

BACKGROUND

Recently, with the advance of sensor technologies, a sensor for acquiring a user's sleep information is under development. A technique which checks for a user's sleep state to induce a sleep in order to help a user to have a deep sleep is being actively researched by incorporating the sensor technology and an information technology (IT).

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an electronic device capable of acquiring user's sleep information and spraying a material capable of inducing a user to sleep by analyzing the sleep information, thereby inducing the user to sleep and helping the user to have a deep sleep, and capable of managing a user's sleep.

In accordance with an aspect of the present disclosure, an electronic device is provided. The electronic device includes a capsule unit configured to contain at least one capsule, a discharge unit configured to discharge a material included in the capsule, a communication unit configured to transmit data to an external device or for receiving data from the external device, and at least one processor configured to receive user state information and bio information from the external device via the communication unit, select at least one capsule in the capsule unit on the basis of the received user state information and bio information, determine a spray amount of a material contained in the selected at least one capsule, and control the discharge unit to spray the material.

In accordance with another aspect of the present disclosure, a method of controlling a capsule of an electronic device is provided. The method includes receiving user state information and bio information from an external device via a communication unit, selecting at least one capsule in a capsule unit on the basis of the received user state information and bio information, determining a spray amount of a material contained in the selected at least one capsule, and spraying the material via a discharge unit.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
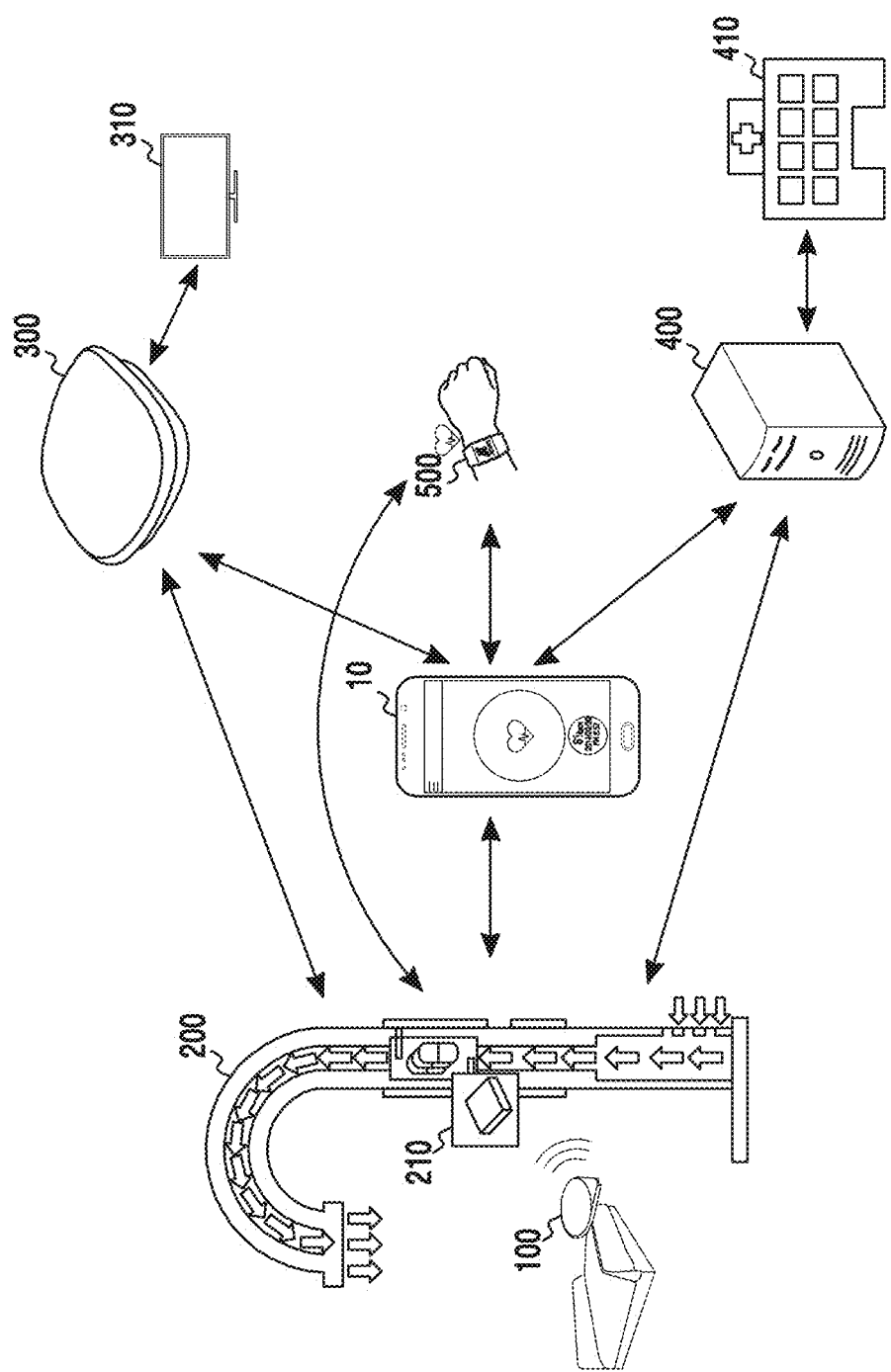
FIG. 1 illustrates a structure of a system according to an embodiment of the present disclosure.

The following description with reference to the accompanying drawings is provided to assist in a comprehensive understanding of various embodiments of the present disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the present disclosure. Accordingly, it should be apparent to those skilled in the art that the following description of various embodiments of the present disclosure is provided for illustration purposes only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the present document, an expression "A or B", "A and/or B", or the like may include all possible combinations of items enumerated together. Although expressions such as "$1^{st}$", "$2^{nd}$", "first", and "second" may be used to express corresponding constitutional elements, it is not intended to limit the corresponding constitutional elements. When a certain (e.g., $1^{st}$) constitutional element is mentioned as being "operatively or communicatively coupled with/to" or "connected to" a different (e.g., $2^{nd}$) constitutional element, the certain constitutional element is directly coupled with/to another constitutional element or can be coupled with/to the different constitutional element via another (e.g., $3^{rd}$) constitutional element.

An expression "configured to" used in the present document may be interchangeably used with, for example, "suitable for", "having the capacity to", "adapted to", "made to", "capable of", or "designed to" in a hardware or software manner according to a situation. In a certain situation, an expressed "a device configured to" may imply that the device is "capable of" together with other devices or components. For example, "a processor configured to perform A, B, and C" may imply a dedicated processor (e.g., an embedded processor) for performing a corresponding operation or a generic-purpose processor (e.g., central processing unit (CPU)) capable of performing corresponding operations by executing one or more software programs stored in a memory device.

In the present document, a heartbeat may mean a heart rate, a pulsation may mean a pulse rate, and a breath may mean a breathing rate.

FIG. 1 illustrates a structure of a system according to an embodiment of the present disclosure.

Referring to FIG. 1, a system according to an embodiment of the present disclosure includes a sleep data (SD) acquisition device 100, an electronic device 200, a user terminal 10, a home hub 300, a wearable device 500, and a service server 400.

The SD acquisition device 100 may be disposed below or above a bed mattress, may detect a heartbeat, breath, movement of a user who has gone to bed, and may output an electrical signal corresponding to the sensed heartbeat, breath, and movement of the user.

The SD acquisition device 100 may transmit information related to the heartbeat, breath, and movement acquired from the user to the electronic device 200 or a different device. The SD acquisition device 100 may transmit at least one of the user's state information and the user's bio information to the electronic device 200 or the different device. The user's state information may include information related to the user's movement, and the user's bio information may include heartbeat and breath information or the like.

The electronic device 200 may perform spraying by placing a capsule including a material capable of inducing the user to sleep to a flow passage through which air passes, thereby inducing the user to sleep. The electronic device 200 may receive user state information, bio information, and user related information from the SD acquisition device 100, the user terminal 10, the home hub 300, the wearable device 500, or the service server 400, may select at least one capsule among a plurality of capsules on the basis of the received information, and may discharge a material included in the selected capsule, thereby inducing the user to sleep and helping the user to have a deep sleep. The electronic device 200 may acquire information related to the user's sleep from the home hub, the wearable device 500, or the service server 400 via the user terminal 10. Further, the electronic device 200 may acquire the information related to the user's sleep directly from the home hub 300, the wearable device 500, or the service server 400 not via the user terminal 10. The information related to the user's sleep may be user information which may have an effect on the sleep. For example, the information related to the user's sleep may include a user's movement, heartbeat, pulsation, body temperature, user's biorhythm index, stress index, medical record, domestic/international travel schedule, media watching information, television (TV) watching information, gaming time, and/or exercise time. However, the information related to the user's sleep is not limited to the aforementioned example, and may include all user information which may have an effect on the user's sleep.

The electronic device 200 may be provided in a form of an air purifier and an air conditioner. Constitutional elements of the electronic device 200 may be included in the air purifier and the air conditioner.

The user terminal 10 may receive the information related to the user's sleep from the home hub 300, the wearable device 500, and the service server 400 to provide visual information to the user, and may transmit the information related to the user's sleep to the electronic device 200. The information related to the user's sleep may be transmitted directly to the electronic device 200 from the home hub 300, the wearable device 500, or the service server 400. Further, the user terminal 10 may receive information regarding a sleep analysis result from the electronic device 200 to provide visual information to the user. For example, at least one of information regarding a user's sleep pattern, a user's sleep state, and a user's sleep time may be visually provided to the user. The user terminal 10 may transmit information regarding an app (or an application) executed by the user and personal information (e.g., schedule information) to the electronic device 200. The user terminal 10 may provide information regarding a capsule included in the electronic device 200 to the user in a visual or auditory manner. The user terminal 10 may be replaced with a different electronic device having communication capability. For example, the user terminal 10 may be a tablet personal computer (PC), a mobile phone, a video phone, an electronic book reader, a desktop PC, a laptop PC, a netbook computer, or the like. However, the present disclosure is not limited thereto.

The home hub 300 may receive usage history information of a different indoor electronic device 310 (e.g., TV, audio, cleaner, washing machine, cooker, dish washer, microwave oven, oven, etc.) by the user and user's movement information and bio information sensed at various indoor locations, and may transmit the information to the electronic device 200 or the user terminal 10. The electronic device 200 may select a capsule and determine a spray amount and spray time of the capsule on the basis of the usage history information of the different electronic device 310, which is transmitted from the home hub 300, and the user's movement information and bio information sensed at various indoor locations.

The wearable device 500 may be attached to a user's body to acquire the user's movement information and exercise information. The wearable device 500 may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device (e.g., an implantable circuit). However, the present disclosure is not limited thereto. The wearable device 500 may transmit the acquired user's movement information and exercise information to the electronic device 200. The electronic device 200 may select a capsule and determine a spray amount and spray time of the capsule on the basis of the user's movement information and exercise information transmitted from the wearable device 500.

The service server 400 may receive service information which can be acquired from an outdoor place 410 of the user. The service information may include, for example, a user's medical record, hotel usage information, flight travel information, train travel information, or the like. The electronic device 200 may receive the service information, and on the basis of the received service information, may select a capsule and determine a spray amount and spray time of the capsule. The electronic device may receive the service information via the user terminal or may receive it directly from the service server. Further, the electronic device 200 may store the received service information into a storage unit 210 in a database manner.

Figure 2A:
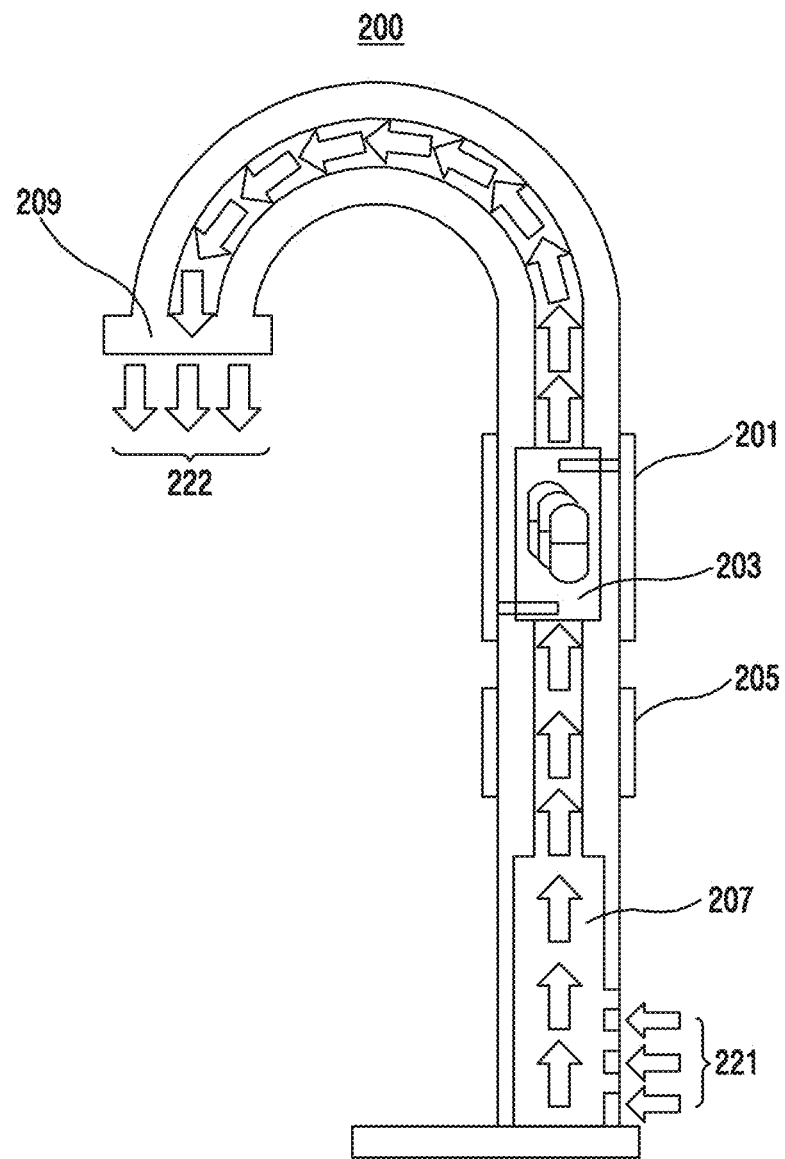
FIGS. 2A and 2B illustrate an electronic device according to various embodiments of the present disclosure.
Figure 2B:
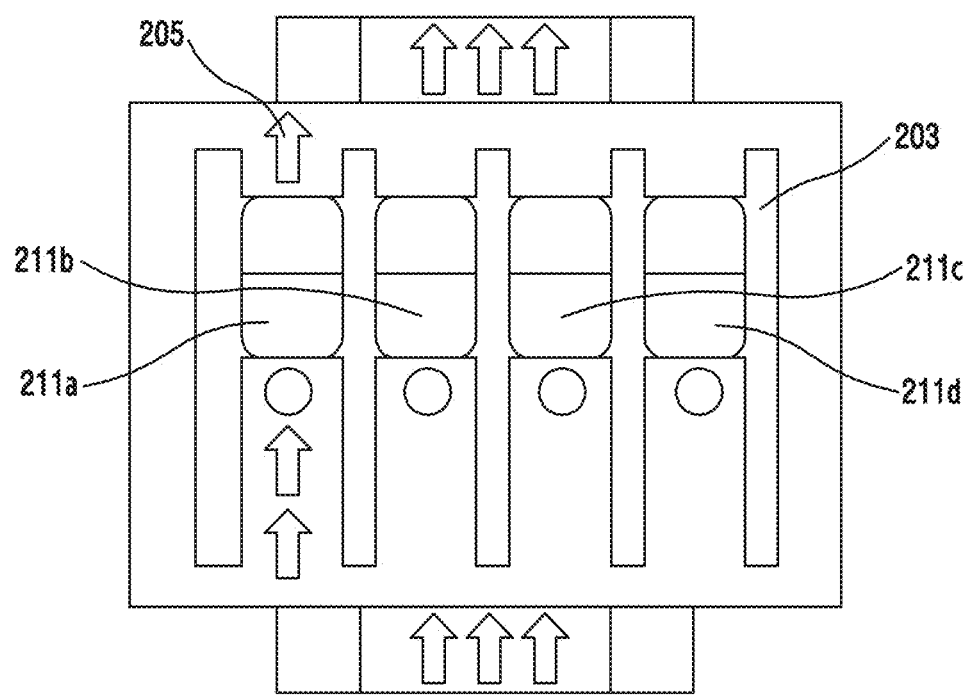

FIGS. 2A and 2B illustrate an electronic device according to various embodiments of the present disclosure.

Referring to FIG. 2A, the electronic device 200 may include a discharge unit 209, a capsule unit 203, a controller 201, a communication unit 205, and a conditioning unit 207. The electronic device 200 has a flow passage tube formed therein, and air may flow through the flow passage tube. The flow passage tube through which the air can flow may be formed inside the electronic device 200. An overall shape of the electronic device may be a tower type or a wall-mount type in which spraying is easily performed on a user who is lying. More specifically, the electronic device may have a downward discharge structure. For example, air may pass through a flow passage tube having a shape of an umbrella handle and formed in an inner portion. However, the shape of the electronic device is not limited thereto. The capsule unit 203 may be formed in a middle portion of the electronic device 200.

The conditioning unit 207 may allow external air of the electronic device 200 to enter into the electronic device 200. The conditioning unit 207 may include at least one of an air cleaning filter and a ventilation fan. The ventilation fan allows the external air to enter into the electronic device 200. Impurities may be removed while the air which enters into the electronic device 200 passes through the air cleaning filter. The impurity-removed air may move to the capsule unit 203 through a flow passage.

The capsule unit 203 may include a capsule container. In one embodiment, the controller 201 may be disposed inside the capsule unit 203. However, the present disclosure is not limited thereto. At least one capsule may be placed (or contained) in the capsule container. The controller 201 may provide control to select at least one capsule so that air passes through the selected capsule, or may spray a material included in the capsule to the air passage tube. While the air passes through the capsule, the material included in the capsule may be spayed into the air passage tube. Further, the controller 201 may adjust a spray amount and spray time of the material included in the capsule.

The discharge unit 209 may be formed at a first side of the electronic device 200 to discharge the air, and air spraying strength (intensity) may be adjusted by the controller 201.

The communication unit 205 may receive user related information from a different indoor electronic device through a home hub. The user related information may include history information regarding the different indoor electronic device (e.g., TV, audio, cleaner, washing machine, cooker, dish washer, microwave oven, oven, etc.) used by the user and user's movement information and bio information sensed at various indoor locations.

The communication unit 205 may receive the user's movement information and exercise information from a user terminal and a wearable device worn by the user.

The communication unit 205 may receive service information which can be acquired from a user's outdoor activity via a service server. The service information may include a user's medical record, prescription information, chronic/serious disease information, constitution information, sleep management information, sleep care service information, hotel usage information, flight travel information, train travel information, time difference information, travel schedule information, hotel customer management information, or the like.

The communication unit 205 may receive indoor or outdoor environment information (e.g., indoor/outdoor temperature, humidity, atmospheric pressure, oxygen concentration, air quality, etc.).

The communication unit 205 may transmit control data capable of controlling a different electronic device (e.g., a lighting device, a sound device, TV, a conditioning device, etc.) to the different electronic device.

External air 221 enters into the electronic device 200 by means of the conditioning unit 207, and may be combined with a material inside the capsule unit 203 while passing through the capsule unit 203, and may be sprayed (see 222) to the outside of the electronic device 200 via the discharge unit 209.

According to an embodiment of the present disclosure, the electronic device 200 may further include an infrared image camera, a microphone, an air quality sensor, an illumination sensor, an oxygen generator, an anion generator, a virus doctor, a lighting device, a sound generating device, or the like. The infrared image camera may sense a motion such as tossing and turning of the user. The microphone may sense a user's snoring sound when the user is sleeping. The air quality sensor may sense a foreign material included in the air. The illumination sensor may sense ambient brightness. However, the present disclosure is not limited thereto.

The electronic device 200 may analyze a user's sleep state and may control the lighting device on the basis of the analysis. For example, on/off or illumination of the lighting device may be adjusted according to the user's sleep state. Further, the electronic device may control the sound device according to the user's sleep state. For example, if it is time for the user to wake up, the electronic device 200 may control the sound device to reproduce pre-set music or other alarm in the sound device.

According to an embodiment, the electronic device may operate without the conditioning device. If the electronic device does not have an additional conditioning device, the capsule unit 203 may be disposed adjacent to the discharge unit 209, and may be implemented in such a manner that the spraying device is coupled to the capsule.

Referring to FIG. 2B, a plurality of capsules 211*a*, 211*b*, 211*c*, and 211*d* are placed (or contained) in the capsule unit 203. Condensate liquid or powder of various properties may be included inside the capsule to help a user's sleep or deep sleep. For example, a tranquilizer, melatonin, growth hormone, a scent material, an aroma material, and a prescription drug may be included. A memory for storing condensate liquid information may be included in the capsule. For example, the memory may store information such as a serial number of the capsule, a usage of the condensate liquid, a name of the condensate liquid, a spray time and spray amount of the condensate liquid, a spray timing of the condensate liquid, a residual of the condensate liquid, or the like. However, the information stored in the memory is not limited thereto.

Air entering the electronic device 200 may receive the condensate liquid or condensate powder included in the capsule while passing through the capsule. When the capsule is selected by the controller 201, the controller 201 may open an air passage to allow the air to flow to the selected capsule, so that the air can pass through the capsule. Alternatively, when the capsule is selected by the controller 201, the condensate liquid or powder may be sprayed through a capsule spraying device to the passage tube which passes through the capsule container. Further, the controller 201 may adjust a spray amount of the capsule through a spray adjusting device.

For example, when the capsule 211*a* is selected by the controller 201, the controller 201 may open a passage connected to a flow passage tube which passes through the capsule container or an inner portion of the capsule 211*a* so that air can flow to the capsule 211*a*. A valve may be placed to the passage, and the controller 201 may control the capsule unit 203 to open or close the valve of the selected capsule. When the capsule 211*b* is selected, the controller may open the passage connected to the capsule 211*b* so that air can flow to the capsule 211*b*.

Figure 3A:
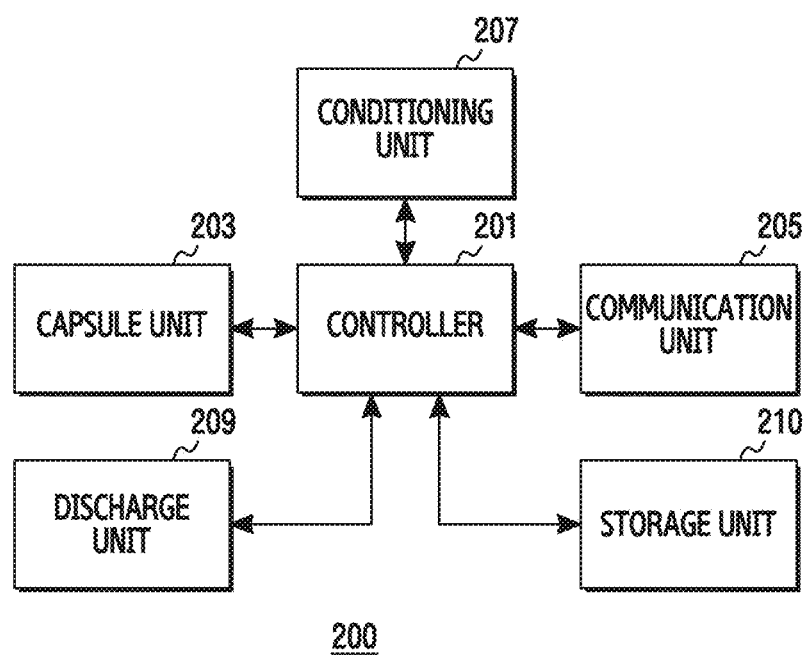
FIG. 3A is a block diagram of an electronic device according to an embodiment of the present disclosure.

FIG. 3A is a block diagram of an electronic device according to various embodiments of the present disclosure.

Referring to FIG. 3A, the electronic device may include the controller 201, the capsule unit 203, the communication unit 205, the conditioning unit 207, the discharging unit 209, and the storage unit 210.

The controller 201 may include one or more of a CPU, an application processor (AP), and a communication processor (CP). The controller 201 may execute an arithmetic operation or data processing related to a control and/or communication of at least one different component of the electronic device 200.

The controller 201 may control a plurality of hardware or software components connected to the controller 201, by driving an operating system or an application program, and may perform a variety of data processing and arithmetic operations. The controller 201 may be implemented with a system-on-chip (SoC). The controller 201 may process an instruction or data, which is received from at least one of different constitutional elements (e.g., a non-volatile memory), by loading the instruction or data to a volatile memory and may store a variety of data in the non-volatile memory.

The controller 201 may provide control to receive user state information and bio information via the communication unit 205, to select at least one capsule in the capsule unit 203 on the basis of the user state information and bio information, to determine a spray amount and spray time of a material included in the capsule, and to spray the material to the outside of the electronic device 200 via the discharge unit 209. The controller 201 may determine the spray time of the material included in the capsule on the basis of the user's state information and bio information. The bio information may include at least one of a heartbeat, a pulsation, and a breath. Further, the controller 201 may determine the user's sleep state on the basis of the received user state information and bio information. The controller 201 may determine a type, spray amount, and spray time of the capsule on the basis of the user's sleep state. The controller 201 may determine the type, spray amount, and spray time of the capsule on the basis of a set value stored in the capsule. The controller 201 may determine the type, spray amount, and spray time of the capsule on the basis of a user's previous sleep pattern stored in the storage unit 210. The controller 201 may receive a user's medical record via the communication unit 205, and may determine the type, spray amount, and spray time of the capsule on the basis of the medical record. The controller 201 may receive a usage history of a user's wearable device or a user terminal via the communication unit 205, and may determine the type, spray amount, and spray time of the capsule on the basis of the usage history of the wearable device and the user terminal. The controller 201 may receive data related to a user's life pattern via the communication unit 205, and may determine the type, spray amount, and spray time of the capsule on the basis of the user's life pattern. The controller 201 may determine the type, spray amount, and spray time of the capsule on the basis of indoor/outdoor climate information. The controller may determine the type, spray amount, and spray time of the capsule on the basis of sleep care information (e.g., history) preferred by the user. The controller may determine the type, spray amount, and spray time of the capsule on the basis of sleep care preference information of a day in which an input is made by the user. Further, the controller 201 may generate data for controlling an external device operatively coupled to the electronic device 200 on the basis of the user's sleep state information, and may transmit control data to the external device via the communication unit 205.

The storage unit 210 may include a volatile and/or non-volatile memory. The storage unit 210 may include an internal memory or an external memory. The internal memory may include, for example, at least one of a volatile memory (e.g., a dynamic random access memory (DRAM), a static RAM (SRAM), a synchronous DRAM (SDRAM), etc.) or a non-volatile memory (e.g., a one time programmable read only memory (OTPROM), a programmable ROM (PROM), an erasable and programmable ROM (EPROM), an electrically erasable and programmable ROM (EEPROM), a mask ROM, a flash ROM, a flash memory, a hard driver, and a solid state drive (SSD)). The external memory may include compact flash (CF), secure digital (SD), micro-SD, mini-SD, extreme digital (xD), multimedia card (MMC), memory stick, etc. The external memory may be operatively or physically connected to the electronic device 200 through various interfaces. The storage unit 210 may store instructions or data related to at least one different constitutional elements of the electronic device 200. According to an embodiment of the present disclosure, the storage unit 210 may store user related information received through the communication unit 205 and information related to a user's sleep analyzed in the electronic device 200.

The communication unit 205 may communicate by being connected to a user terminal, a home server, a wearable device, or a service server through wireless communication or wired communication.

The wireless communication may include cellular communication using at least one of long term evolution (LTE), LTE advanced (LTE-A), code division multiple access (CDMA), wideband CDMA (WCDMA), universal mobile telecommunications system (UMTS), wireless broadband (WiBro), global system for mobile communications (GSM), etc. According to one embodiment, the wireless communication may include, for example, at least one of Wi-Fi, Bluetooth, Bluetooth low energy (BLE), ZigBee, near field communication (NFC), magnetic secure transmission, radio frequency (RF), body area network (BAN), etc.

According to an embodiment of the present disclosure, the wireless communication may include a global navigation satellite system (GNSS). The GNSS may be, for example, global positioning system (GPS), global navigation satellite system (GLONASS), BeiDou navigation satellite system (hereinafter, "BeiDou") or Galileo, the European global satellite-based navigation system, etc.

The wired communication may include at least one of universal serial bus (USB), high definition multimedia interface (HDMI), recommended standard-232 (RS-232), power-line communication, plain old telephone service (POTS), etc.

The communication unit 205 may include a cellular module, a Wi-Fi module, a Bluetooth module, a GNSS module, an NFC module, and an RF module. The cellular module may provide a voice call, a video call, a text service, an internet service, or the like through a communication network. According to an embodiment of the present disclosure, the cellular module may identify and authenticate the electronic device 200 in the communication network by using a subscriber identity module (e.g., a subscriber identity module (SIM) card). The cellular module may include a CP. At least some (e.g., two or more) of the cellular module, the Wi-Fi module, the Bluetooth module, the GNSS module, and the NFC module may be included in one integrated chip (IC) or IC package. The RF module may transmit/receive a communication signal (e.g., an RF signal). The RF module may include a transceiver, a power amp module (PAM), a frequency filter, a low noise amplifier (LNA), an antenna, or the like. According to another embodiment of the present disclosure, at least one of the cellular module, the Wi-Fi module, the Bluetooth module, the GNSS module, and the NFC module may transmit/receive an RF signal via a separate RF module. The SIM may include a card including the SIM or an embedded SIM, and may include unique identification information (e.g., an integrated circuit card identifier (ICCID)) or subscriber information (e.g., an international mobile subscriber identity (IMSI)).

The communication unit 205 may receive the user's state information and bio information from an SD acquisition device. The communication unit 205 may receive state information, bio information, an indoor device usage history, or the like at an indoor location of a user via the home server. The communication unit 205 may receive the user's state information, bio information, and a wearable device usage history from the wearable device and the user terminal. The communication unit 205 may receive a user's medical record, user's travel related information, user's schedule information, or sleep care service information from the service server.

The capsule unit 203 may include a capsule container, a capsule controller, and a spray adjuster. A plurality of capsules may be placed in the capsule container. The capsule container may control a flow of air which passes through a passage tube. The capsule controller may include a valve system, and may open or close a valve under the control of the controller 201 to block the flow of air so that the air can pass through the capsule or cannot pass through the capsule. Alternatively, the controller may provide control such that capsule condensate liquid or powder is sprayed or not sprayed to the passage tube which passes through the capsule container. The spray adjuster may adjust a spray amount and spray time of the condensate liquid inside the capsule under the control of the controller 201. In one embodiment, the capsule controller may be included in the controller 201.

The conditioning unit 207 may include at least one of a ventilation fan and an air cleaning filter. Due to a rotation of the ventilation fan, external air of the electronic device may compulsorily enter into the electronic device 200. The controller 201 may adjust a rotation count of the ventilation fan to adjust an amount of air which enters into the electronic device 200. The air cleaning filter may filter impurities included in the air so that clean air enters into the electronic device. The discharge unit is formed at a first side of the electronic device 200 and may adjust a spray amount under the control of the controller 201.

Figure 3B:
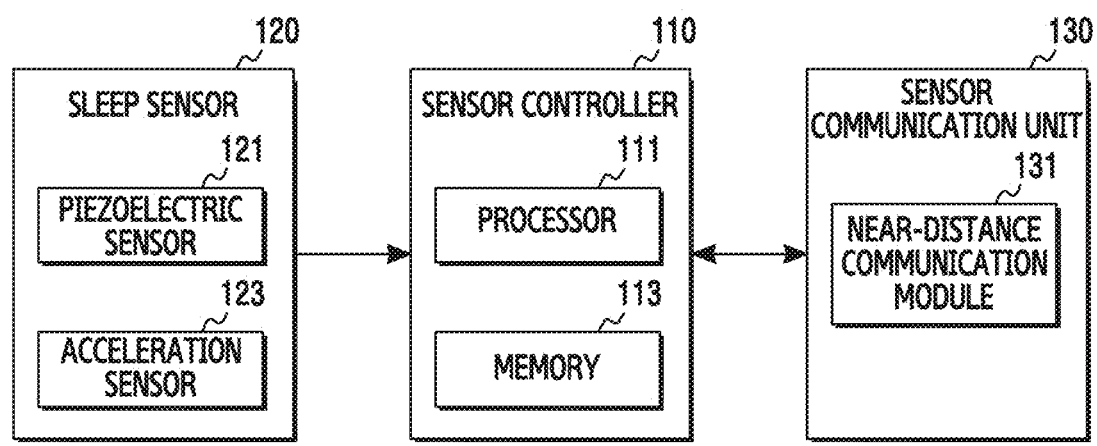
FIG. 3B is a block diagram of a sleep data acquisition device according to an embodiment of the present disclosure.

FIG. 3B is a block diagram of an SD acquisition device according to various embodiments of the present disclosure.

Referring to FIG. 3B, the SD acquisition device 100 may include a sleep sensor 120, a sensor communication unit 130, and a sensor controller 110.

The sleep sensor 120 may detect a heartbeat, breath, and movement of a user who has gone to bed, and may output to the sensor controller 110 an electrical signal corresponding to the sensed heartbeat, breath, and movement of the user.

The sleep sensor 120 may include a piezoelectric sensor 121 for sensing pressure caused by the user's heartbeat, breath, and movement and for outputting an electric signal corresponding to the sensed pressure. The piezoelectric sensor 121 uses a piezoelectric effect in which electrical polarization is generated in a crystal surface when force is applied to a crystal. The piezoelectric sensor 121 generates alternating current voltage while applying the pressure, and generates a vibration when the alternating current voltage is supplied.

When the piezoelectric sensor 121 is pressed by the user's heartbeat, breath, and movement, the piezoelectric sensor 121 may output an electrical signal corresponding to the pressure applied to the piezoelectric sensor 121.

In another example, the sleep sensor 120 may include an acceleration sensor 123 for sensing a vibration caused by the user's heartbeat, breath, and movement and for outputting an electrical signal corresponding to the sensed vibration.

The acceleration sensor 123 is a sensor for measuring a change of speed per unit time. When the acceleration sensor 123 moves or vibrates due to the user's heartbeat, breath, and movement, the acceleration sensor 123 may output an electrical signal corresponding to the movement or the vibration.

However, the sleep sensor 120 does not necessarily include both of the piezoelectric sensor 121 and the acceleration sensor 123. According to a designer's choice, the sleep sensor 120 may include the piezoelectric sensor 121 or the acceleration sensor 123.

The sensor communication unit 130 may include a near-distance communication module 131 for exchanging data with respect to the user terminal 200.

The near-distance communication module 131 may communicate with a communication target by using various communication schemes. For example, the near-distance communication module 131 may communicate with the communication target by using a Wi-Fi communication scheme (Institute of Electrical and Electronics Engineers (IEEE) 802.11), a Bluetooth communication scheme (IEEE 802.15.1), a ZigBee communication scheme (IEEE 802.15.4), or the like.

However, the near-distance communication module 131 does not have to employ all of the Wi-Fi communication scheme, the Bluetooth communication scheme, and the ZigBee communication scheme, and thus may employ at least one of the Wi-Fi communication scheme, the Bluetooth communication scheme, and the ZigBee communication scheme.

The sensor controller 110 may include a memory 113 for storing/remembering a program and data and a processor 111 for processing data and for controlling the sleep sensor 120 and the sensor communication unit 130 according to the program stored in the memory 113.

The memory 113 may store a control program or control data for controlling an operation of the SD acquisition device 100, or may remember SD acquired via the sleep sensor 120.

The memory 113 may include a volatile memory such as an SRAM, a DRAM, or the like and a non-volatile memory such as a ROM, an EPROM, an EEPROM, a flash memory, or the like.

The volatile memory is a memory in which remembered data is lost when power is off, and may temporarily remember a program and data. For example, the volatile memory may remember a control program and control data, or may remember the SD acquired by the sleep sensor 120.

The non-volatile memory is a memory in which stored data can be maintained even if power is off, and may store a program and data semi-permanently. For example, the non-volatile memory may store a control program and control data for controlling an operation of the SD acquisition device 100.

The processor 111 may process the SD which is input from the sleep sensor 120 according to the control program and control data stored in the memory 113, and may transmit the SD to the user terminal 200 via the sensor communication unit 130.

For example, the processor 111 may acquire an electrical signal which is output by the sleep sensor 120 at every pre-set time, and may generate the SD by digitalizing the acquired electrical signal. The processor 111 may output the SD and the control signal to the sensor communication unit 130 so that the sensor communication unit 130 transmits the SD to the user terminal 200.

As described above, the sensor controller 110 may control operations of the sleep sensor 120 and sensor communication unit 130 included in the SD acquisition device 100. It may be interpreted that an operation of the SD acquisition device 100 to be described below may be performed under the control of the sensor controller 110.

Figure 4A:
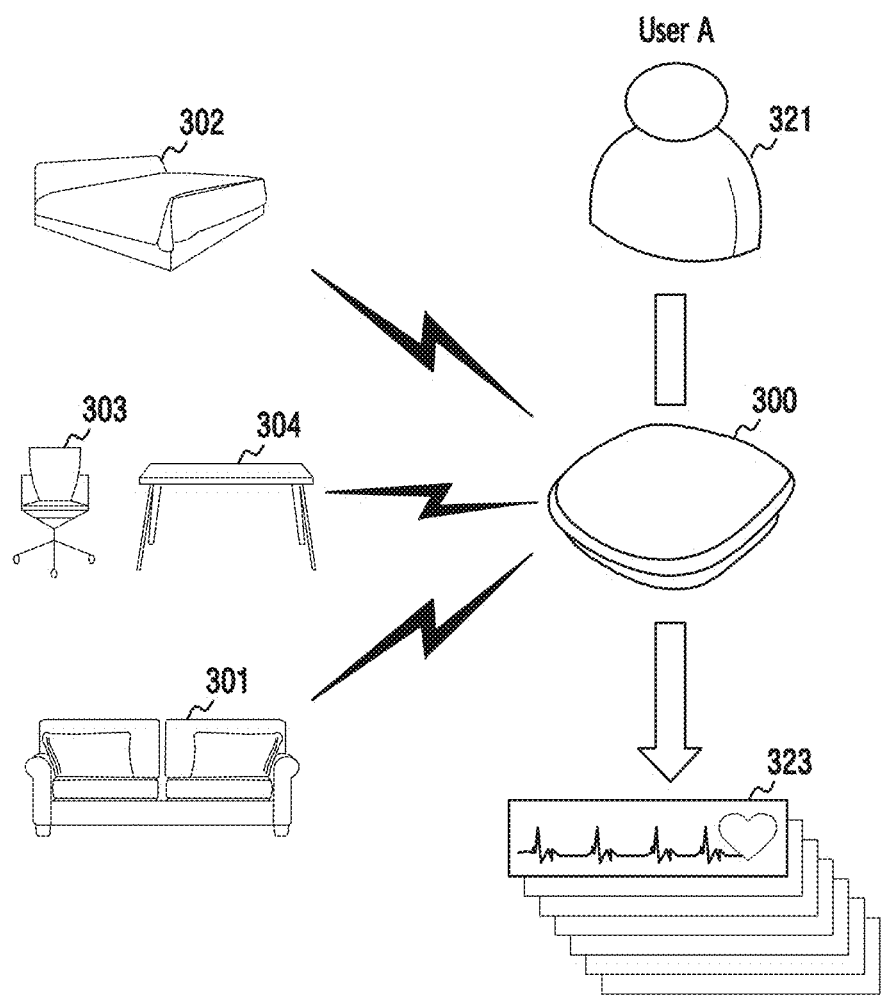
FIGS. 4A and 4B illustrate examples of obtaining user related information in an indoor environment by an electronic device according to various embodiments of the present disclosure.
Figure 4B:
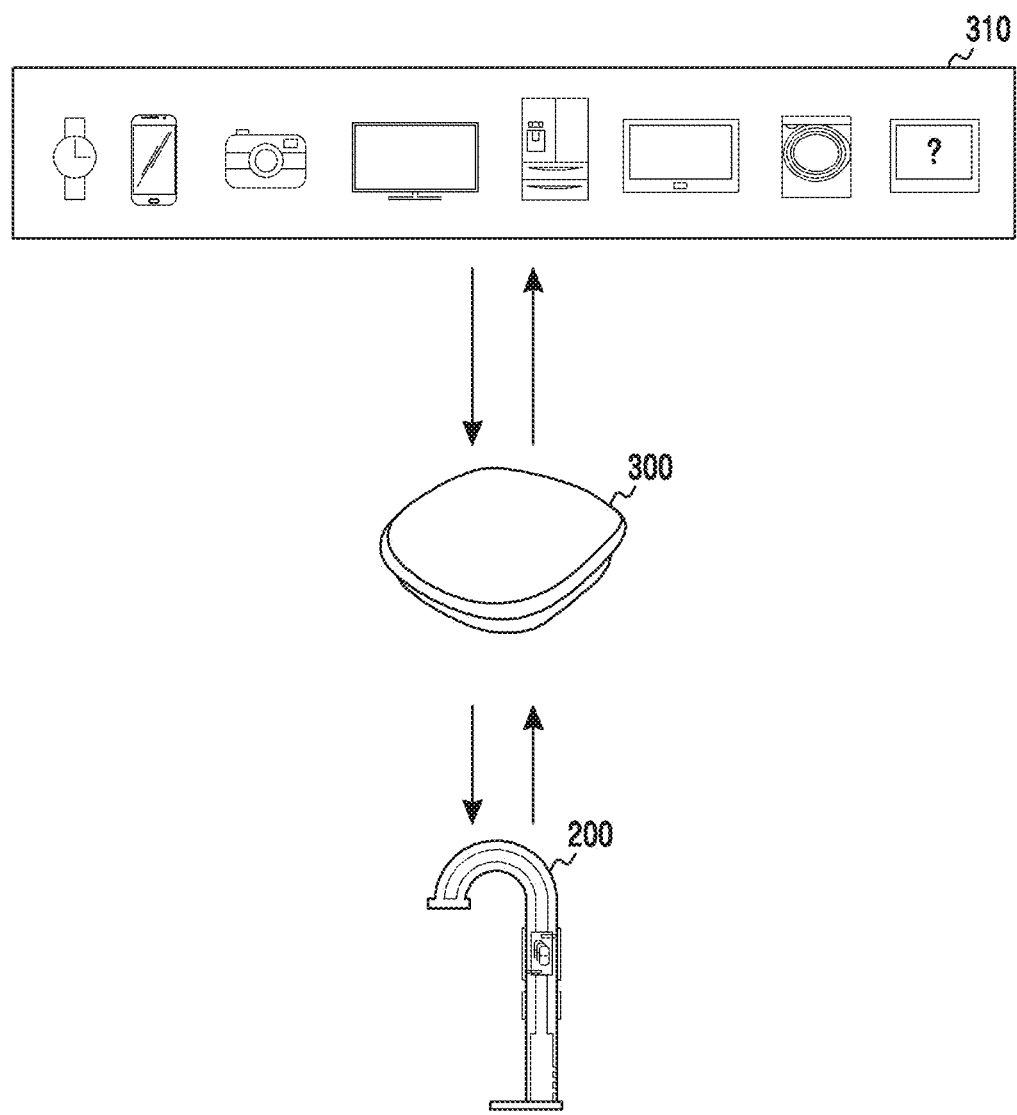

FIGS. 4A and 4B illustrate examples of obtaining user related information in an indoor environment by an electronic device according to various embodiments of the present disclosure.

Referring to FIG. 4A, the home hub 300 may receive the user's state information and bio information from various sources 301, 302, 303, and 304 placed in the indoor environment. The SD acquisition device 100 may be attached to the sources (objects) 301, 302, 303, and 304, and the home hub 300 may receive the user's state information and bio information via the SD acquisition device 100. The SD acquisition device 100 may sense not only information related to a user's sleep but also the user's state information and bio information via a piezoelectric sensor and an acceleration sensor, and may transmit the sensed data to the home hub 300 via the communication module. According to implementations, the SD acquisition device 100 may be replaced with a different sensing device.

The SD acquisition device 100 may be placed to the bedroom bed 302, study chair 303, study table 304, and living room sofa 301 used by the user, and thus may frequently acquire user's state information and bio information to transmit the information to the electronic device 200 via the home hub 300. The bio information may include information regarding a heartbeat, a breath, and a body temperature. The state information may include the user's sleep state information and user's posture information. For example, when the user lies down on the bed to get a sleep, the SD acquisition device 100 may acquire the user's movement information, user's posture information, heartbeat information, and sleep state information, and may transmit the information to the home hub 300. When the user sits on the study chair to read a book, the SD acquisition device 100 may acquire the user's movement information, posture information, and heartbeat information, and may transmit the information to the home hub 300. When the user sits on the living room sofa, the SD acquisition device 100 may acquire the user's movement information, posture information, and heartbeat information, and may transmit the information to the home hub 300.

The home hub 300 may transmit the user's state information and bio information acquired at locations of the various sources to the electronic device 200. The electronic device 200 may store the user's state information and bio information received from the home hub 300 into a storage unit. In this case, the electronic device 200 may store the user's state information and bio information in a database manner together with a time at which the information is acquired. The electronic device 200 may determine the user's state information and bio information acquired concurrently as information of the same user. The electronic device 200 may divide and group the user's state information and bio information acquired from the home hub 300 placed in the indoor environment for each user on the basis of an electrocardiogram pattern acquired from a wearable device worn by the user. For example, the electronic device 200 may acquire a unique electrocardiogram pattern of a user A via a wearable device worn by the user A 321. The electronic device 200 may form one group 323 by distinguishing state information and bio information corresponding to the user A among a plurality of pieces of user state information and bio information stored in the storage unit by using the unique electrocardiogram pattern of the user A.

Referring to FIG. 4B, the home hub 300 may acquire data from various indoor electronic devices 310. The home hub 300 may transmit the acquired data to the electronic device 200, and the electronic device 200 may acquire a usage history of the indoor electronic devices from the received data. The electronic device 200 may provide sleep related information to the user on the basis of the usage history of the indoor electronic devices. The electronic device 200 may recognize whether there is a sleep disturbing factor from the received usage history of the electronic devices, and may provide the user with a presence of sleep recommendation information and the sleep disturbing factor. For example, if the user uses a user terminal, then app data, content usage details, or the like acquired in the user terminal is transmitted to the home hub 300, and the home hub may retransmit this to the electronic device. The app data may be data acquired from an app execution history and an app execution. For example, if a calendar app is executed, the app data may be schedule data, and the electronic device 200 may select a capsule and adjust a spray amount and a spray time on the basis of the schedule data. In another example, if the user excessively watches media by using the user terminal, the electronic device 200 may acquire a media watching time of the user from the user terminal, and on the basis of the media watching time of the user, may notify the user to stop watching the media or give a warning, or may select a capsule capable of helping the user to sleep or to have a deep sleep and adjust a spray amount and spray time of the capsule.

Further, the user terminal may transmit the app data and the content usage details directly to the electronic device 200.

Figure 5:
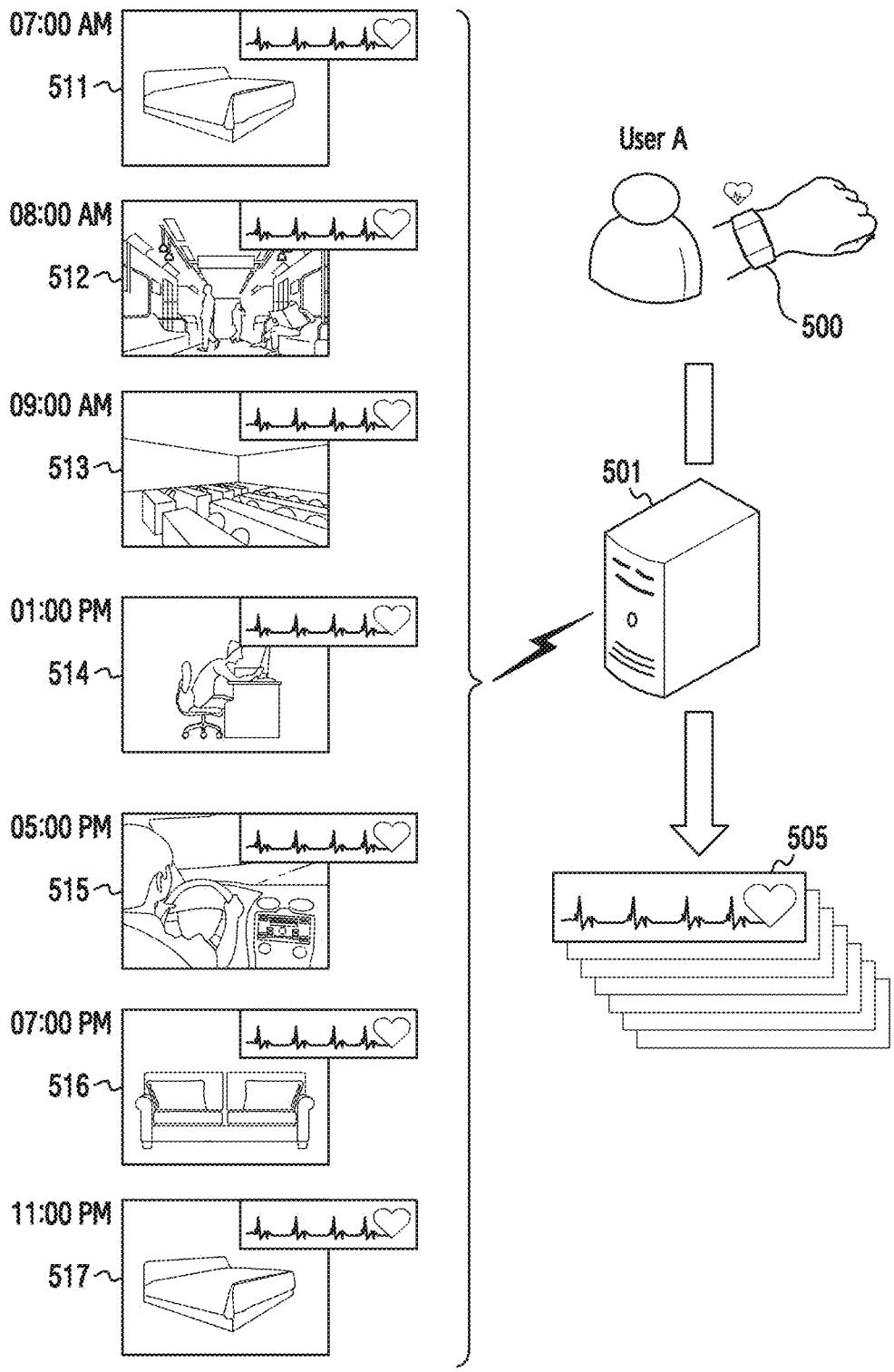
FIG. 5 illustrates an example of obtaining user related information in an outdoor environment by an electronic device according to an embodiment of the present disclosure.

FIG. 5 illustrates an example of obtaining user related information in an outdoor environment by an electronic device according to various embodiments of the present disclosure.

Referring to FIG. 5, the user related information may be bio information acquired from a user when the user is in the outdoor environment. For example, it may be user's heartbeat, posture, breath, and body temperature information acquired in the outdoor environment.

Referring to FIG. 5, a wearable device 500 and a service server 501 are illustrated. If the user does outdoor activities while wearing the wearable device 500, various outdoor electronic devices may collect user's bio information. The various outdoor electronic devices may transmit the collected user's bio information and time information of the collected bio information to the service server 501. The service server 501 may store the received user's bio information and time information in a database manner. The service server 501 may receive user's heartbeat information from the wearable device 500 worn by the user, and on the basis thereof, may search for user's bio information stored in the service server 501 and may group the search result as the user's bio information, thereby acquiring user's bio information per time. For example, as indicated by 511, if a user A wakes up at 7 in the morning to go to work, a sensor placed to a bed may transmit bio information, time information, and ID information of the user A to the service server 501. According to implementations, information transmitted to the service server 501 may include a unique ID of a device which acquires bio information. As indicated by 512, if the user A sits in a subway at 8 o'clock, user A's bio information collected from a sensor placed to a seat in the subway may be transmitted to the service server 501 together with time information and device ID information. As indicated by 513, if the user A has a lesson in a seminar room at 9 o'clock, a sensor placed to a chair of the seminar room may transmit user A's bio information, time information, and ID information to the service server. As indicated by 514, if the user A works while sitting on a chair at 1 o'clock, a sensor placed to the chair may transmit user A's bio information, time information, and ID information to the service server 501. As indicated by 515, if the user A leaves the office at 5 o'clock by using a car, a sensor placed to a chair of the car may transmit user A's bio information, time information, and ID information to the service server 501. As indicated by 516, if the user A watches TV while sitting on a sofa at 7 o'clock, a sensor placed to the sofa may transmit user A's bio information, time information, and ID information to the service server 501. As indicated by 517, if the user A sleeps on a bed at 11 o'clock, a sensor placed to the bed may transmit user A's bio information, time information, and ID information to the service server 501. The service server 501 may receive heartbeat related information of the user A from the wearable device 500 worn by the user A, and on the basis thereof, may form a group 505 by classifying bio information of the user A among bio information data stored in the service server 501. The electronic device 200 may receive grouped user A's bio information from the service server, and on the basis thereof, may select a capsule and determine a spray amount and spray time of the capsule.

Figure 6:
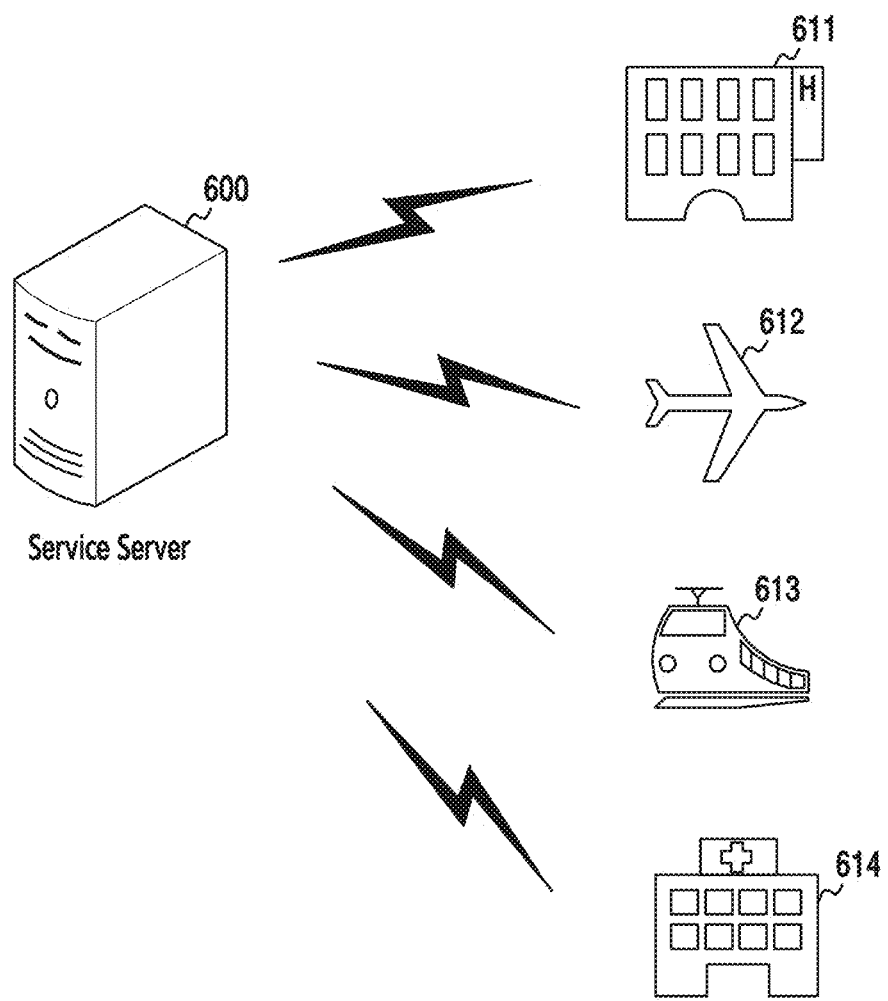
FIG. 6 illustrates an example of obtaining user related information by an electronic device by using an external server according to an embodiment of the present disclosure.

FIG. 6 illustrates an example of obtaining user related information by an electronic device by using an external server according to various embodiments of the present disclosure.

Referring to FIG. 6, a service server 600 is illustrated. The service server 600 may collect user related service information. The user related service information may be information related to a service previously used by a user. The service server may transmit the collected user related service information to the electronic device 200. The electronic device 200 may select a capsule on the basis of the user related service information received from the service server 600, and may determine a spray amount and spray time of the selected capsule.

For example, when the user stays in a hotel 611, the information may be hotel stay information. The hotel stay information may include a hotel location, a hotel stay duration, a check-in time, a check-out time, or the like. The service server 600 may receive user's hotel stay information from a hotel server, and may transmit the information to the electronic device 200. The electronic device 200 may select a capsule on the basis of the user's hotel stay information, and may determine a spray amount and spray time of the selected capsule. The electronic device 200 may determine that the user has come back from travel on the basis of information regarding a location of a hotel in which the user stayed and a hotel stay duration, and may select a capsule capable of decreasing travel fatigue and determine a spray amount and spray time of the capsule.

When the user has returned from a business trip, the service server 600 may receive user's flight boarding time and arrival time information stored in an airline server, and may transmit the information to the electronic device 200. The electronic device 200 may select a capsule on the basis of the user's flight boarding time and arrival time information, and may determine a spray amount and spray time of the selected capsule. The electronic device 200 may find out a region to which the user travels and a flight time on the basis of information regarding an airplane 612 used by the user, and on the basis of this, may select a suitable capsule so that the user can have a deep sleep and may determine a spray amount and spray time of the capsule.

When the user has come back from a travel by using a train 613, the service server 600 may receive user's train boarding time and arrival time information stored in a server of a train company, and may transmit the information to the electronic device 200. The electronic device 200 may select a capsule on the basis of the user's train boarding time and arrive time information, and may determine a spray amount and spray time of the selected capsule. The electronic device 200 may find out a region to which the user travels and a train usage time on the basis of information regarding a train used by the user, and may select a capsule capable of decreasing user's fatigue and may determine a spray amount and spray time of the capsule.

The service server 600 may collect a user's medical record from a server of a hospital 614, and may transmit the medical record to the electronic device 200. The medical record may include a user's medical treatment record, a disease name, and a prescription. The electronic device 200 may select a capsule on the basis of the user's medical record, and may determine a spray amount and spray time of the selected capsule. The electronic device 200 may select a capsule according to the prescription included in the medical record, and may determine a spray amount and spray time of the capsule.

Figure 7:
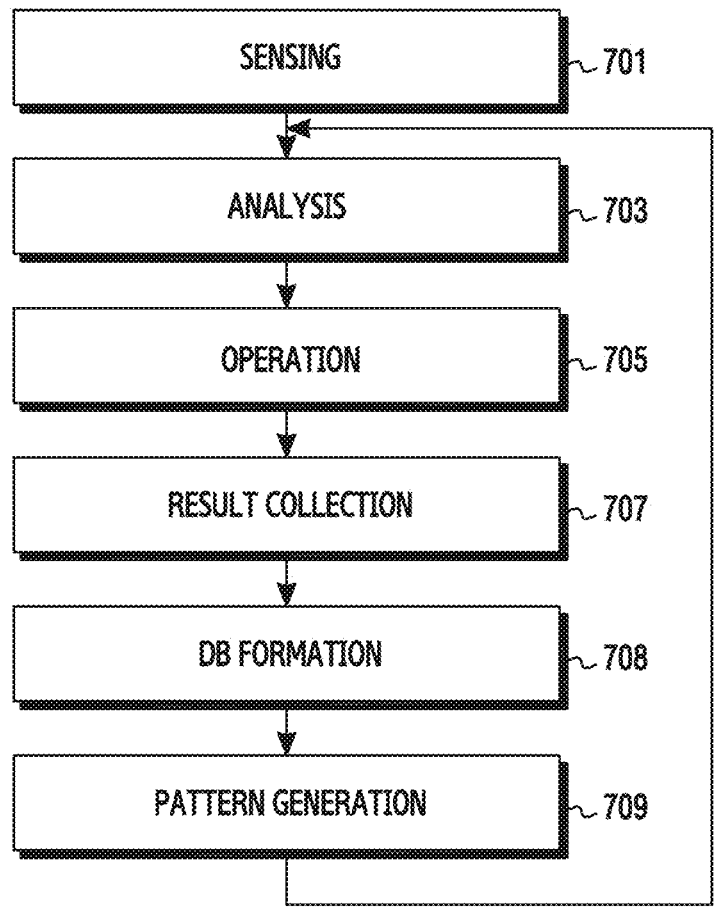
FIG. 7 illustrates a procedure in which an electronic device analyzes and processes user related information according to an embodiment of the present disclosure.

FIG. 7 illustrates a procedure in which an electronic device analyzes and processes user related information according to various embodiments of the present disclosure.

Referring to FIG. 7, in operation 701, the electronic device 200 may sense user related information via an SD acquisition device. The electronic device 200 may receive information sensed by the SD acquisition device.

The user related information may include a user's heartbeat, posture, body temperature, a user's sound, and a user action type. The user action type may be, for example, information regarding whether a user is eating or whether the user is reading. Further, the electronic device 200 may sense the user related information via a home hub, a wearable device, a user terminal, or a service server.

In operation 703, the electronic device 200 may analyze the user related information sensed via the SD acquisition device, the home hub, the wearable device, or the service server to determine a user's health state, sleep state, life habit, or the like. For example, the electronic device 200 may determine whether the user is healthy, whether the user satisfies recommended sleep hours during one day or a specific period, whether there is no abnormality in a sleep pattern, whether there is no negative sleep habit, whether the user had a deep sleep, and whether the user has a sleep at a determined time.

In operation 705, the electronic device 200 may select a capsule on the basis of the user related information received from the SD acquisition device, the home hub, the wearable device, the user terminal, or the service server, and may determine a spray amount and spray time of the selected capsule to spray a martial included in the capsule. For example, the electronic device 200 may analyze the user related information, and if it is determined that the user requires sleep and is unhealthy, may select a capsule for inducing the sleep, a capsule for helping restoration of mind and body, and a capsule for medicine treatment, and may spray a material included in the selected capsule. A spray amount and spray time of the capsule may be determined according to a result analyzed in the electronic device 200, or may be determined according to information which is read from a memory included in the capsule. The electronic device 200 may transmit control data capable of controlling neighboring devices to the neighboring devices on the basis of the analyzed result. For example, the electronic device 200 may determine the user's sleep state and health state on the basis of the user related information received from the SD data acquisition device, the home hub, the wearable device, the user terminal, or the service server, and may control brightness and on/off of a lighting device, on/off of a sound device, and driving of a conditioning device. When it is determined as a time at which the user has to wake up, the electronic device 200 may adjust illumination to be bright and may reproduce music in a sound device. When it is determined that a user's body temperature is low, the electronic device 200 may control a conditioning device to increase a room temperature. Further, when it is determined that the user is sleeping, the electronic device 200 may stop the driving of the conditioning device so that the user's body temperature is not decreased.

In operation 707, the electronic device 200 may compare data before and after spraying of the capsule. For example, a palmarosa oil has a disinfection and antifebrile effect. The electronic device 200 may spray the palmarosa oil included in the capsule and compare user's body temperatures before and after spraying of the capsule to adjust a spray amount of the capsule.

In operation 708, the electronic device 200 may store the collected user related information in a database, and may group the collected user related information for each collected place or time. For example, the electronic device 200 may search the user related information collected randomly and stored in a storage unit to find the user related information as heartbeat information acquired from a wearable device worn by a specific user, and may group specific user related information.

In operation 709, the electronic device 200 may analyze the user related information stored in the database and thus may determine a specific user's sleep pattern, life habit, and main daily routine. For example, the electronic device 200 may analyze the user's sleep information sensed via the SD acquisition device while the user is asleep, and thus may determine a user's sleep pattern. The electronic device 200 may recognize a user's wake-up time on the basis of the user related information received via the home hub or the SD acquisition device, and may recognize which electronic device is driven by the user after the wake-up, thereby determining the user's life habit. The electronic device 200 may recognize a user's main daily routine on the basis of user's service usage information received via the service server. For example, the electronic device 200 may determine that the user is scheduled to receive a medical treatment in hospital from the user's schedule information and medical information.

Figure 8:
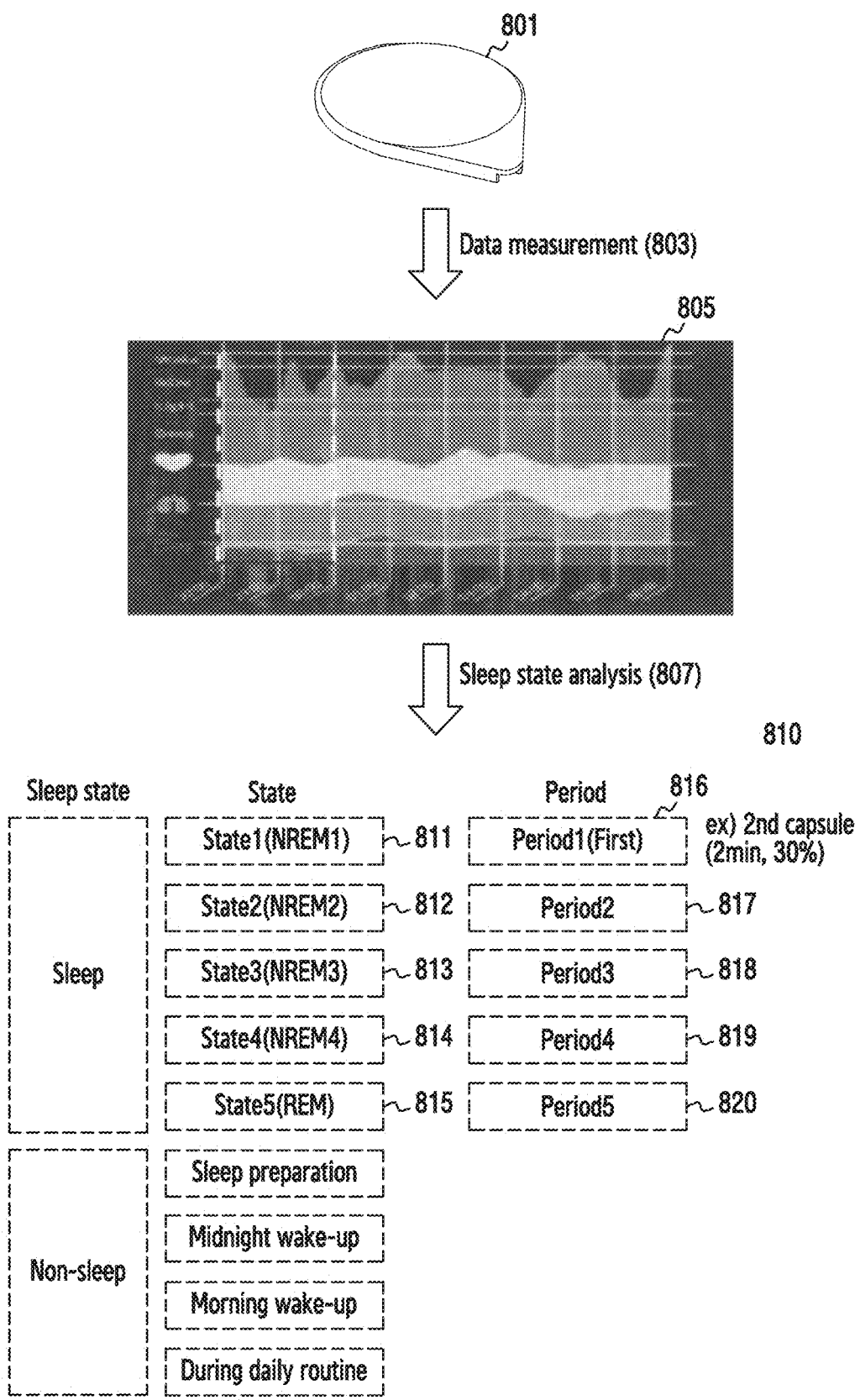
FIG. 8 illustrates a procedure of recognizing a user's sleep state on the basis of user related information received by an electronic device according to an embodiment of the present disclosure.

FIG. 8 illustrates a procedure of recognizing a user's sleep state on the basis of user related information received by an electronic device according to various embodiments of the present disclosure.

Referring to FIG. 8, in operation 803, an SD acquisition device 801 may sense user's state information and bio information and transmit the information to the electronic device 200. In operation 805, the electronic device 200 may analyze the received user's state information and bio information to measure a user's sleep state on a real time basis. In operation 807, the electronic device may analyze the user's sleep state from the measured data to determine at which stage a user currently is among sleep stages.

The electronic device may determine whether the user is currently in a sleep state or a non-sleep state on the basis of information transmitted from the sleep state acquisition device.

The non-sleep state may be divided into a sleep preparation stage, a midnight wake-up stage, and a wake-up stage. The electronic device may determine whether the user is on a bed simply in a non-sleep state during a daily routine or is in the non-sleep state.

The electronic device may determine a user's sleep state time on the basis of recent average sleep start time information. In general, a non-sleep state until one hour before the recent average sleep start time may be determined as a non-sleep state for preparing a sleep. Accordingly, if a sleep preparation time exceeds an average sleep preparation time, the electronic device may induce the sleep by compulsorily turning off lights, and may determine as a sleep disorder when the user fails to enter a sleep stage even after turning off the lights. In this case, the electronic device may spray a sleep inducing material such as a stress relief, nerve stability care, melatonin, or the like, or may spray a sleeping pill prescribed for the user. Herein, the stress relief and nerve stability care is not limited to the spraying of the capsule material, and thus a stress relief method which is preferred by the user or input from the user may be used such as sound, illumination, and oxygen generation, anion emission, or the like.

The electronic device 200 may determine whether the user is currently in a rapid eye movement (REM) sleep state or a non-REM (NREM) sleep state on the basis of the user's bio information (e.g., heartbeat, breath, movement, etc.) transmitted from the SD acquisition device. The electronic device 200 may analyze the user's bio information to determine whether the user's sleep reaches the REM sleep stage or releases from the REM sleep stage, and may determine a time of reaching the REM sleep stage and a time of releasing from the REM sleep stage and store the determined time into the storage unit. If it is determined that the user is in the NREM sleep state, the electronic device 200 may divide the NREM sleep state into a plurality of stages 811, 812, 813, 814, and 815 according to a sleep depth, and may determine a specific sleep period to which a current user's sleep belongs among sleep periods 816, 817, 818, 819, and 820.

The electronic device 200 may select at least one capsule according to an analysis result, and may determine a spray amount and spray time of the selected capsule. For example, if it is determined that the user's sleep state corresponds to the NREM sleep stage II 812 and the first period 816, the electronic device 200 may spray a material included in a $2^{nd}$ capsule in amount of about 30% for 2 minutes.

Figure 9A:
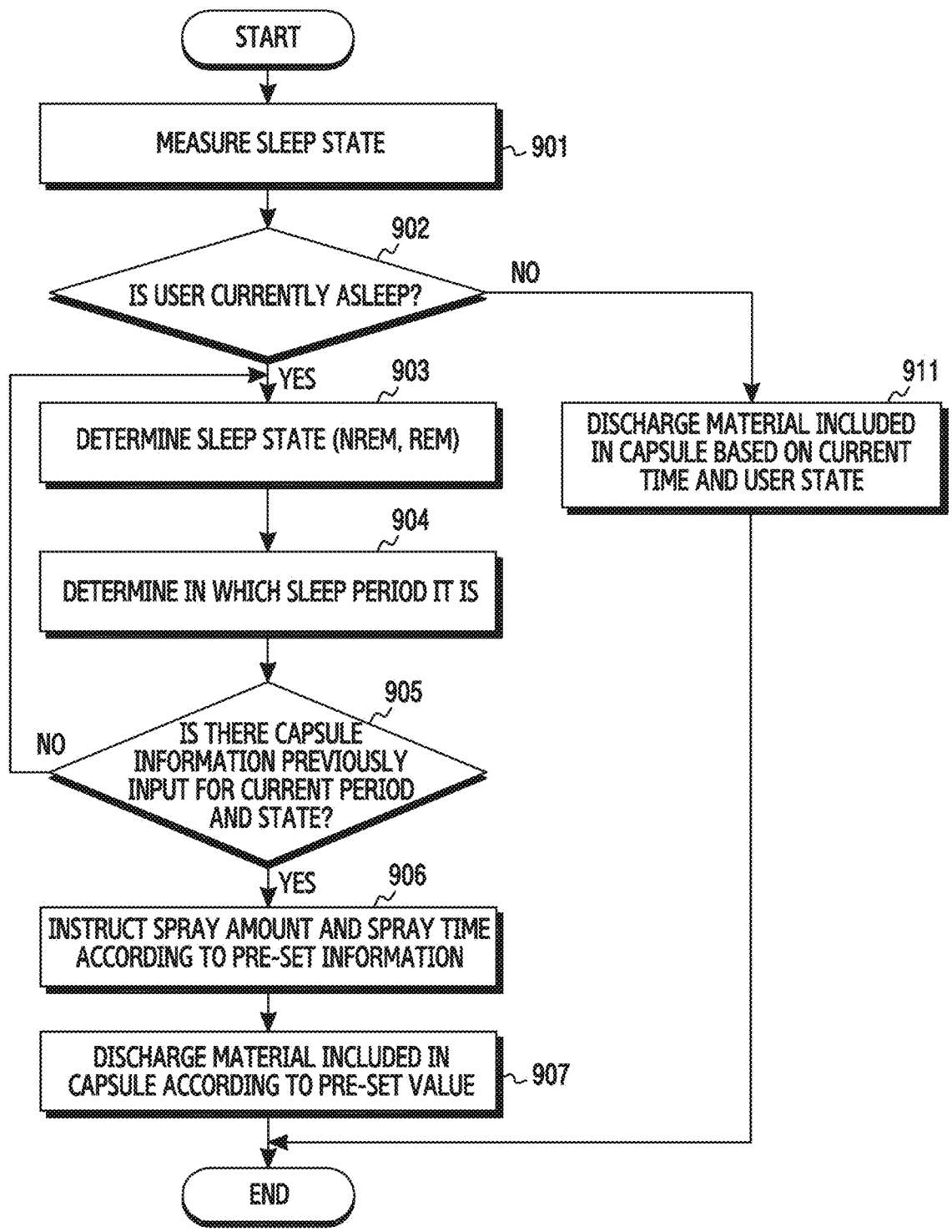
FIG. 9A illustrates an example of spraying a material included in a capsule on the basis of user's state information and bio information in an electronic device according to an embodiment of the present disclosure.
Figure 9B:
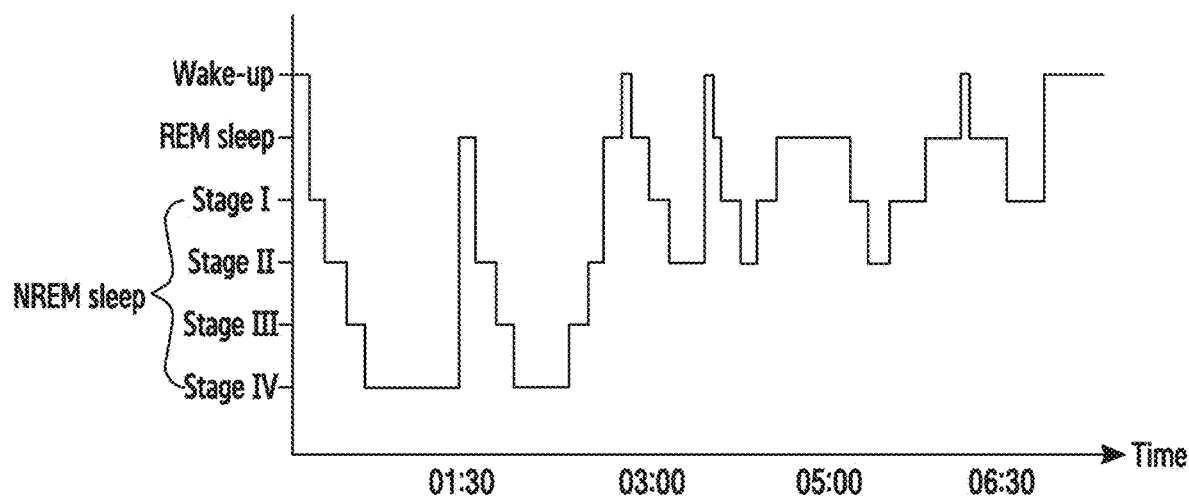
FIG. 9B illustrates an example of a user's sleep period according to an embodiment of the present disclosure.

FIG. 9A illustrates an example of spraying a material included in a capsule on the basis of user's state information and bio information in an electronic device according to various embodiments of the present disclosure. FIG. 9B illustrates an example of a user's sleep period according to an embodiment of the present disclosure.

Referring to FIG. 9A, in operation 901, the electronic device 200 may measure a sleep state. The electronic device 200 may measure a user's sleep state on the basis of bio information transmitted from an SD acquisition device. The bio information may include a user's heartbeat, breath, and movement. In operation 902, the electronic device 200 may analyze the user' bio information to determine whether a user is currently asleep.

When the user goes to bed, the SD acquisition device may sense a heartbeat, breath, and movement of the user who goes to bed, and may transmit SD corresponding to the user's heartbeat, breath, and movement to the electronic device 200 or a user terminal (e.g., the user terminal 10 of FIG. 1). Further, the electronic device 200 may determine a time at which the user goes to bed on the basis of the SD. For example, before the user goes to bed, the SD acquisition device may sense a vibration which is caused by a user's daily routine and is less than a threshold, but the SD acquisition device may interpret the vibration less than the threshold as a meaningless noise, and thus may not transmit data corresponding to the vibration less than the threshold to the electronic device 200. As a result, before the user goes to bed, the user terminal may not be able to receive SD from the SD acquisition device. However, the present disclosure is not limited thereto.

On the other hand, if the user goes to bed, the SD acquisition device may sense a vibration greater than or equal to the threshold. The SD acquisition device may transmit SD corresponding to the vibration greater than or equal to the threshold to the electronic device.

If the SD starts to be received from the SD acquisition device, the electronic device 200 may determine that the user goes to bed, and may determine a time at which the SD starts to be received as a time at which the user goes to bed.

Further, when the user goes to sleep, the SD acquisition device may sense a heartbeat, breath, and movement of the user who goes to sleep, and may transmit SD corresponding to the user's heartbeat, breath, and movement to the electronic device 200. Further, the electronic device may determine a time at which the user goes to sleep on the basis of the SD.

When the user goes to bed, the user does not always fall asleep as soon as the user goes to bed. After going to bed, the user may not be able to fall asleep for as little as several minutes or as long as several hours. Therefore, the time at which the user goes to bed may be different from the time at which the user goes to sleep.

Further, a heartbeat, breath, and movement of a user who is awake is different from a heartbeat, breath, and movement of a user who is asleep. More specifically, it is widely known that the user's heartbeat and breath are decreased in number while sleeping.

Therefore, upon receiving the SD from the SD acquisition device, the electronic device 200 may determine whether the user is awake or asleep on the basis of the user's heartbeat, breath, and movement, and may determine a time at which the user goes to sleep on the basis of a result of determining whether the user is awake or asleep.

If it is determined that the user is asleep, in operation 903, the electronic device 200 may determine a user's sleep state.

For example, whether the user is currently in an REM sleep state or an NREM sleep state may be determined.

While the user is asleep, the SD acquisition device may sense the user's heartbeat, breath, and movement at every pre-set time, and may transmit SD corresponding to the user's heartbeat, breath, and movement to the electronic device 200.

On the basis of SD of the user who is asleep, the electronic device 200 may determine a user's sleep stage and whether the user wakes up from a conscious or unconscious state.

As widely known, it is not that a person immediately falls into a deep sleep and thereafter suddenly wakes up but that a human sleep consists of a specific stage and period. For example, as shown in FIG. 9B, after the person goes to sleep, the person gradually enters a deep sleep stage, and thereafter enters a shallow sleep stage, and then returns to the deep sleep state. The human sleep is a repetition of these stages.

As is well known, such a human sleep is divided into an REM sleep and an NREM sleep, and the NREM sleep may be divided into four stages in total.

The REM sleep occupies approximately 20 to 25% of a total sleep. During the REM sleep, a specific brainwave is observed, a muscle tension is decreased to a minimum level, and a specific REM is observed.

Further, a human brain is active during the REM sleep such as dreaming or the like. In addition, a heart rate and a breathing rate are significantly changed during the REM sleep.

As described above, the NREM sleep may be divided into a stage I, a stage II, a stage III, and a stage IV. In general, a sleep of the stages III and IV is referred to as a deep sleep, and a sleep of the stages I and II is referred to as a swallow sleep. The deep sleep occupies approximately 15 to 20% of the total sleep.

During the NREM sleep, the muscle tension is decreased, and a physical movement is also decreased. In addition, a human brain activity is significantly decreased during the NREM sleep.

In particular, the heart rate and the breathing rate are decreased during the NREM sleep in comparison with a non-sleep state, and are relatively regular.

As such, since the human sleep exhibits a specific heartbeat, breath, and movement in each stage, the electronic device may determine a user's sleep stage on the basis of SD exhibiting a heartbeat, breath, and movement of a user who is asleep.

For example, the electronic device 200 may determine whether a user's sleep reaches the REM sleep stage or is released from the REM sleep stage, and may determine/store a time of reaching the REM sleep stage and a time of releasing from the REM sleep.

For another example, the electronic device 200 may determine whether the user's sleep reaches a deep sleep stage (stages III and IV) of the NREM sleep or is released from the deep sleep stage, and may determine/store a time of reaching the deep sleep stage and a time of releasing from the deep sleep stage.

In operation 904, the electronic device 200 may determine the user's current sleep period. The electronic device may determine the NREM sleep stages I to IV and the REM sleep as one period, and may determine the user's current sleep period. In operation 905, the electronic device 200 may identify whether there is previously input capsule information for a current user's sleep period and state, and if there is capsule information corresponding thereto, in operation 906, the electronic device 200 may determine a spray amount and spray time of a capsule according to pre-set information, and may spray a material included in the capsule. The pre-set information may be directly set by the user, may be set via a memory included in the capsule, or may be set on the basis of data transmitted from a service server. For example, when the user goes to hospital to receive treatment and a doctor prescribes a capsule including a sleep related material (e.g., a sleep-inducing tranquilizer, melatonin, a deep sleep supplement, a health supplement, growth hormone, an air freshener, an aroma material, a medicine, or the like), information regarding the capsule may be transmitted to the electronic device 200 via the service server. On the basis of the transmitted capsule information, if a capsule usage condition is met, the electronic device 200 may select the capsule, and may determine a spray amount and spray time of the capsule according to the prescription. In operation 907, the electronic device 200 may spray the material included in the capsule according to a pre-set value, and may discharge the material to the outside via a discharge unit. If there is no previously input capsule information, returning to operation 902, the electronic device 200 may continuously sense the user's sleep state via the SD acquisition device.

If it is determined in operation 902 that the user is not asleep, in operation 911, the electronic device 200 may discharge the material included in the capsule on the basis of a current time and a user's state. For example, if the current time is 6:00 p.m., the electronic device 200 may determine that it is too early for the user to go to bed and thus may not perform an additional capsule discharge operation. If the current time is 11:00 p.m., the electronic device 200 may determine that it is a time for the user to go to bed, may select a capsule capable of inducing a user's sleep, and may spray a material included in the capsule. Further, the electronic device 200 may determine whether it is a time for the user to go to bed on the basis of a user's ordinary life pattern.

It is known that a sleeping person wakes up from a conscious or unconscious state. For example, referring to FIG. 9B, the person enters a wake-up stage during an REM sleep. Further, in the wake-up stage, the person may wake up from the conscious or unconscious state. During the waking up, a heart rate and a breathing rate are increased, and a movement becomes active.

Therefore, the electronic device 200 may determine whether the user wakes up from the sleep on the basis of SD indicating a heartbeat, breath, and movement of the user who is asleep. For example, the electronic device 200 may determine whether the user wakes up while sleeping, and may determine/store a wake-up time. Further, if the user falls asleep within a reference time (e.g., 30 minutes) after waking up, the electronic device may determine that the user continues to sleep, and may determine/store again a time at which the user falls asleep.

After waking up from the sleep, the user who completes the sleep may get out of bed. When the user wakes up and gets out of bed, the electronic device 200 may determine whether the user wakes up or the user gets out of bed on the basis of SD received from the SD acquisition device. Further, the electronic device 200 may determine/store a time at which the user wakes up and a time at which the user gets out of bed.

As described above, the electronic device 200 may acquire the user's sleep information on the basis of the SD. The electronic device 200 may acquire sleep time information such as a time at which the user goes to bed, a time at which the user falls asleep, a time at which the user changes a sleep stage, a time at which the user temporarily wakes up while sleeping, a time at which the user falls asleep again while sleeping, a time at which the user wakes up, a time at which the user gets out of bed, or the like.

Further, the electronic device 200 may generate user's sleep summary information on the basis of user's sleep time information. For example, the electronic device 200 may acquire the sleep summary information such as a total sleep time, a time until the user is asleep, the number of times of waking up while sleeping, a sleep efficiency, a deep sleep time, an REM sleep time, or the like on the basis of the user's sleep time information.

When the user wakes up in the middle of the night, the electronic device 200 may select a capsule for inducing a user's sleep and may spray a sleep inducing material. When the user wakes up in the morning or when a wake-up time arrives, the electronic device 200 may control a lighting device to interrupt the user's sleep by increasing brightness of illumination, or may control a sound device so that the user can wake up. Further, the electronic device 200 may select a capsule and spray a material included in the capsule according to information which is pre-set by the user.

Figure 10:
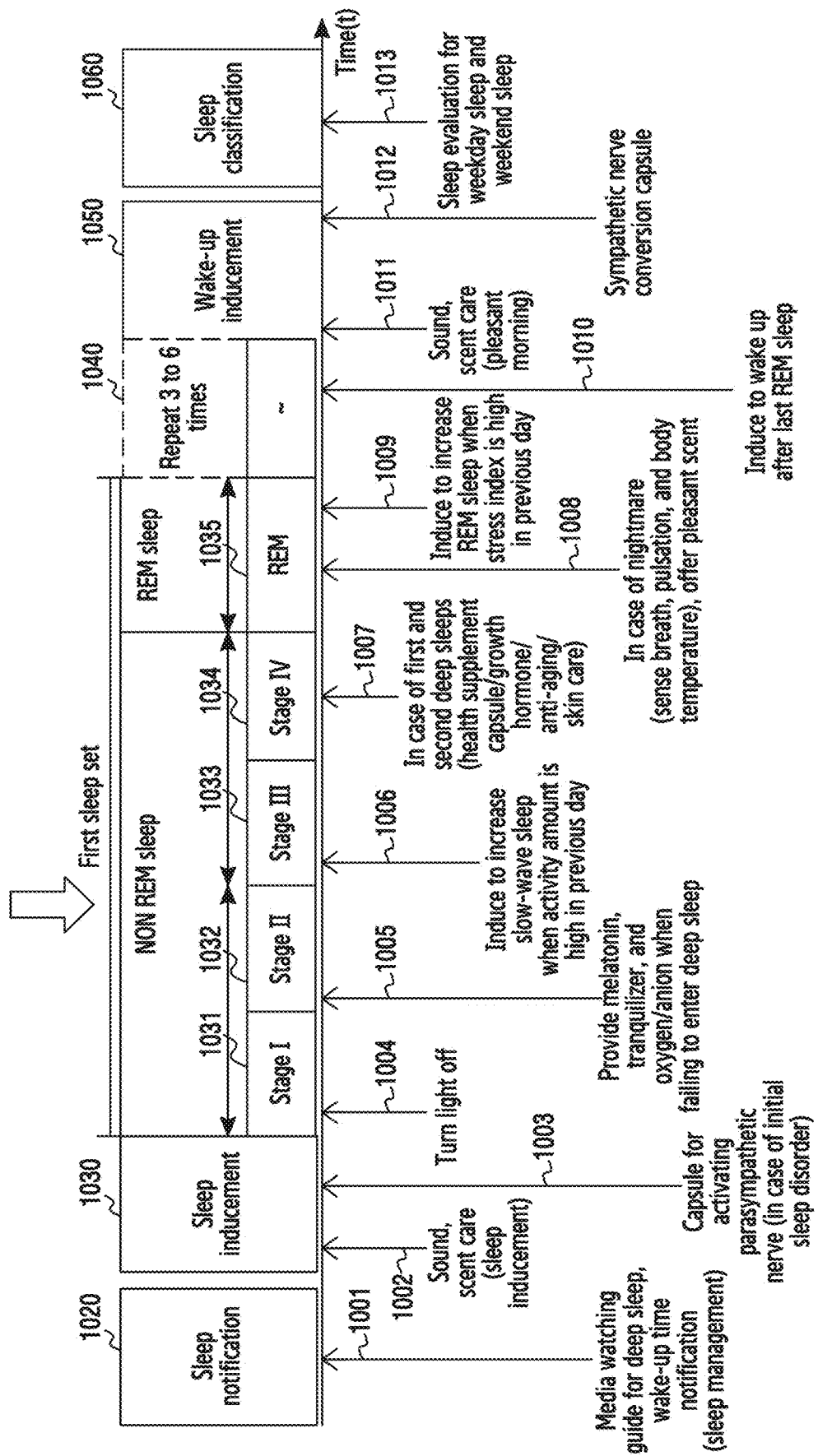
FIG. 10 illustrates an operation of an electronic device according to a sleep stage according to an embodiment of the present disclosure.

FIG. 10 illustrates an operation of an electronic device according to a sleep stage according to an embodiment of the present disclosure.

Referring to FIG. 10, the electronic device 200 may divide the sleep stage into a sleep notification 1020, a sleep inducement 1030, a wake-up inducement 1050, and a sleep classification 1060, and may perform a corresponding operation according to each stage. However, the division of the sleep stage is not limited thereto.

In a process of the sleep notification 1020, the electronic device 200 may provide the user with information for a deep sleep (see 1001). For example, the electronic device 200 may provide the user with a media watching guide for the deep sleep and a sleep time notification to start a user's sleep management. A process of the sleep inducement 1030 may include NREM sleep stages 1031, 1032, 1033, and 1034 and an REM sleep stage 1035. The NREM sleep stage may further include the stage I 1031, the stage II 1032, the stage III 1033, and the stage IV 1034. The NREM sleep stage I 1031 and stage II 1032 may correspond to an initial sleep stage, and the NREM sleep stage III 1033 and stage IV 1034 may correspond to a deep sleep stage. The NREM sleep stages I to IV and the REM sleep may constitute one sleep period, and there may be a repetition stage 1040 in which the sleep period is repeated.

In a process of the sleep inducement, the electronic device 200 may use a sound for inducing a sleep or a capsule for spraying a material having a scent (see 1002) to induce the sleep. In the NREM sleep stage I 1031, the electronic device may control a lighting device to adjust brightness of illumination or may turn off the illumination to make a room dark (see 1004). The electronic device 200 may measure a user's heartbeat, breath, movement, or the like via the SD acquisition device to identify whether the user is asleep. If it is determined in the NREM sleep stage II 1032 that the user fails to enter the deep sleep, the electronic device 200 may spray a material for overcoming a sleep disorder (see 1003). For example, the material for overcoming the sleep disorder may be a prescription sleeping pill, a tranquilizer, melatonin, aroma, or the like. Alternatively, the electronic device 200 may control a different electronic device such as an oxygen generator and an anion generator to induce the user's sleep (see 1005).

If it is determined that an amount of user's activity is high on the basis of the user related information collected via the service server, the wearable device, or the user terminal, in the NREM sleep stage III 1033, the electronic device 200 may select a related capsule to induce a slow-wave sleep (see 1006) or may control a related neighboring device.

In the NREM sleep stage IV 1034, the electronic device 200 may select a capsule including a health supplement material, growth hormone, an anti-aging material, or a skin care material and may spray a material included in the capsule (see 1007).

When it is identified in the REM sleep stage 1035 that the user has a nightmare, the electronic device 200 may select a capsule including a pleasant scent material and spray the material included in the capsule (see 1008). The electronic device 200 may use a user's breath, pulsation, and body temperature to identify whether the user has the nightmare. Further, when the user has a high stress index of a previous day in the REM sleep stage 1035, the electronic device 200 may select a capsule for inducing an increase in the REM sleep and spray a material included in the capsule (see 1009). The user's stress index may be collected via the service server, the wearable device, and the user terminal. The electronic device 200 may identify the number of repetitions 1040 (e.g., 3 to 6) of the sleep period on the basis of user's SD, and may induce the user to wake up after a last REM sleep (see 1010). In a process of the wake-up inducement 1050, the electronic device 200 may use a sound for inducing the user to wake up or may use a capsule for spraying a material having a scent to induce the user to wake up (see 1011). According to implementations, the electronic device 200 may select a sympathetic nerve conversion capsule (see 1012) in the process of the wake-up inducement 1050. Further, the electronic device 200 may evaluate a user's sleep state of weekdays and sleep state of weekends in a process of the sleep classification 1060 (see 1013).

The electronic device 200 may select at least one stage among user's sleep stages according the user related information received from the service server, and may select a capsule corresponding to the selected sleep stage and spray a material included in the capsule. For example, if it is determined that the user snores, the electronic device 200 may select a capsule including an aroma material and spray the material included in the capsule in the NREM sleep stage. If it is determined that the user has sleep apnea, the electronic device 200 may select a capsule including a material for inducing a wake-up and spray the material included in the capsule, or may control a neighboring sound device or a sound device to induce the user to wake up. If it is determined that the user drank too much in a previous day, the electronic device 200 may select a capsule including an oriental raisin material and spray the material included in the capsule in the NREM sleep stage. If the user returns from an overseas travel, the electronic device 200 may manage a sleep rhythm to allow the user to adjust a time difference. If it is determined that the user is being managed for a body rhythm, the electronic device 200 may suggest the user a sleep schedule and may manage the user's sleep. If the user wants a short sleep, the electronic device 200 may induce to wake up after having a deep sleep one time. The electronic device 200 may adjust the user's sleep on the basis of date information. For example, if it is determined as a weekday on the basis of the user's date information, the electronic device 200 may provide the user a notification for recommending a sleep according to a weekday's sleep result.

Figure 11:
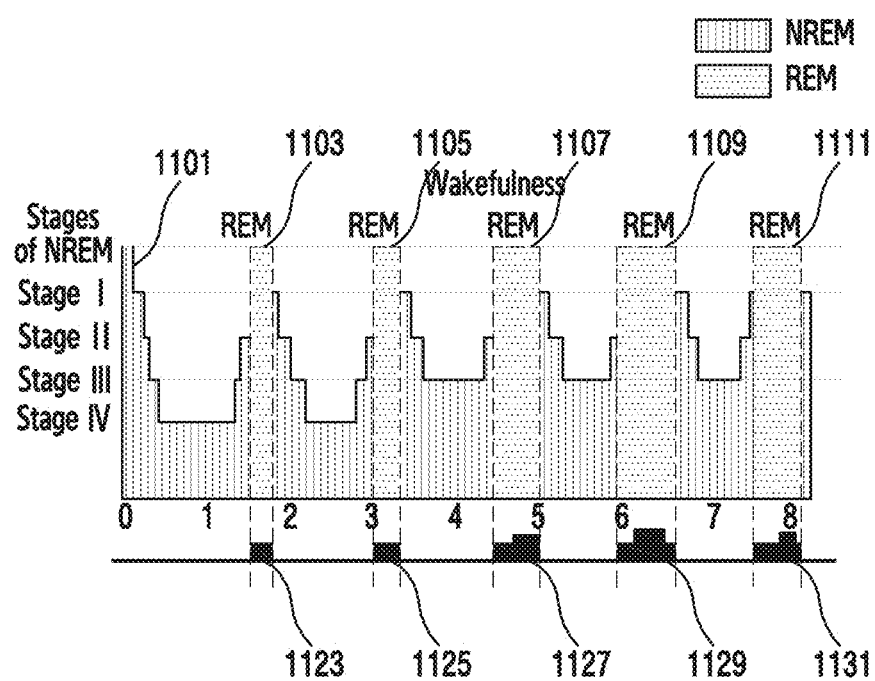
FIG. 11 illustrates an example of determining a user's sleep pattern and controlling spraying of a capsule on the basis of the sleep pattern in an electronic device according to an embodiment of the present disclosure.

FIG. 11 illustrates an example of determining a user's sleep pattern and controlling spraying of a capsule on the basis of the sleep pattern in an electronic device according to various embodiments of the present disclosure.

Referring to FIG. 11, a graph is illustrated in which an NREM sleep stage 1101 and REM sleep stages 1103, 1105, 1107, 1109, and 1111 are repeated. The electronic device 200 may determine that a user took exercise in a previous day via a service server, and may select a capsule (hereinafter, a muscle recovery capsule) including a material which is helpful in muscle recovery and spray the material included in the capsule in an REM sleep stage to recover user's muscle. For example, the electronic device 200 may spray a material included in a muscle recovery capsule 1123 during the first REM sleep stage 1103 of a user. The electronic device 200 may spray a material included in a muscle recovery capsule 1125 during the REM sleep stage II 1105 of the user. The electronic device 200 may spray a material included in muscle recovery capsule 1127 during the REM sleep stage III 1107 of the user. The electronic device 200 may spray a material included in a muscle recovery capsule 1129 during the REM sleep stage IV 1109 of the user. The electronic device 200 may spray a material included in a muscle recovery capsule 1131 during the REM sleep stage V 1111 of the user.

Figure 12:
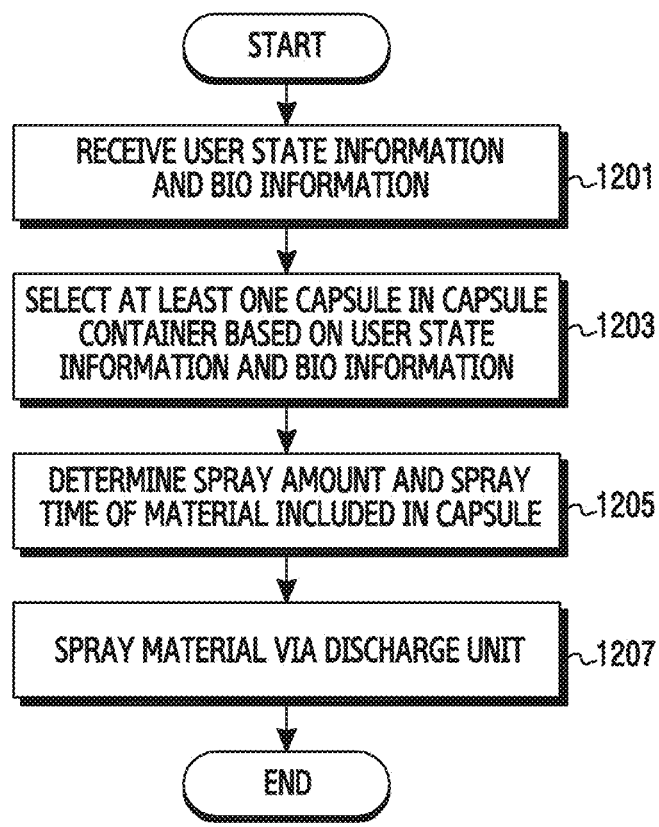
FIG. 12 illustrates a procedure of controlling a capsule of an electronic device according to an embodiment of the present disclosure.

FIG. 12 illustrates a procedure of controlling a capsule of an electronic device according to various embodiments of the present disclosure.

Referring to FIG. 12, in operation 1201, the electronic device 200 may receive user's state information and bio information. The user's state information may be, for example, information related to a user's movement. The user's bio information may include at least one of a user's heartbeat, pulsation, and breath. The electronic device 200 may acquire the user's state information and the user's bio information via an SD acquisition device.

In operation 1203, the electronic device 200 may select at least one capsule in a capsule container on the basis of the user's state information and bio information. The electronic device 200 may determine a user's sleep state on the basis of the user's state information and bio information. The user's sleep state may include the sleep stage described in FIGS. 9A and 9B. The electronic device 200 may determine a type of a capsule on the basis of the user's sleep state.

In operation 1205, the electronic device 200 may determine a spray amount of a material included in the capsule. The electronic device 200 may determine a spray amount and spray time of the capsule on the basis of the user's sleep state. Further, the electronic device 200 may determine the type, spray amount, and spray time of the capsule on the basis of a set value stored in the capsule. The electronic device 200 may determine the type, spray amount, and spray time of the capsule according to a previous sleep pattern of the user. The electronic device 200 may receive a user's medical record via a communication unit, and may determine the type, spray amount, and spray time of the capsule on the basis of the medial record. The medical record may be collected via a servicer server. The electronic device may receive user customized sleep care service information via the communication unit, and may determine the type, spray amount, and spray time of the capsule on the basis of the user customized information.

In operation 1207, the electronic device 200 may discharge a material included in the capsule via a discharge unit. The material included in the capsule may be a material which may help a user's health and sleep capability, or may be stored in the capsule in a liquid or powder form. Since the procedure of selecting the capsule and spraying the material included in the capsule in the electronic device 200 is the same as described in FIGS. 2A, 2B, 3A, and 3B, details thereof will be omitted herein.

Figure 13:
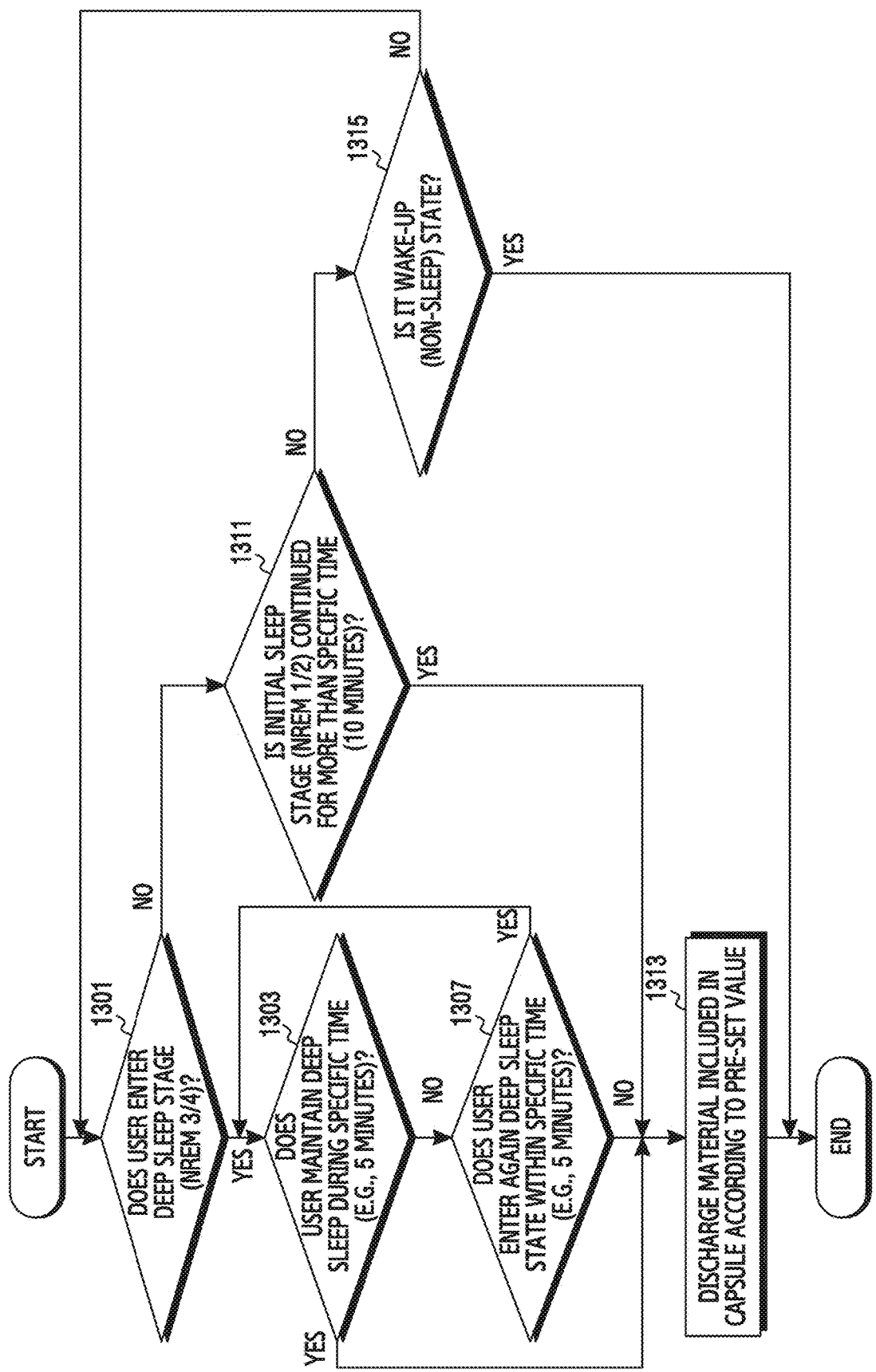
FIGS. 13 and 14 illustrate an example of selecting a capsule and spraying a material included in the capsule on the basis of user's sleep state in an electronic device according to various embodiments of the present disclosure.
Figure 14:
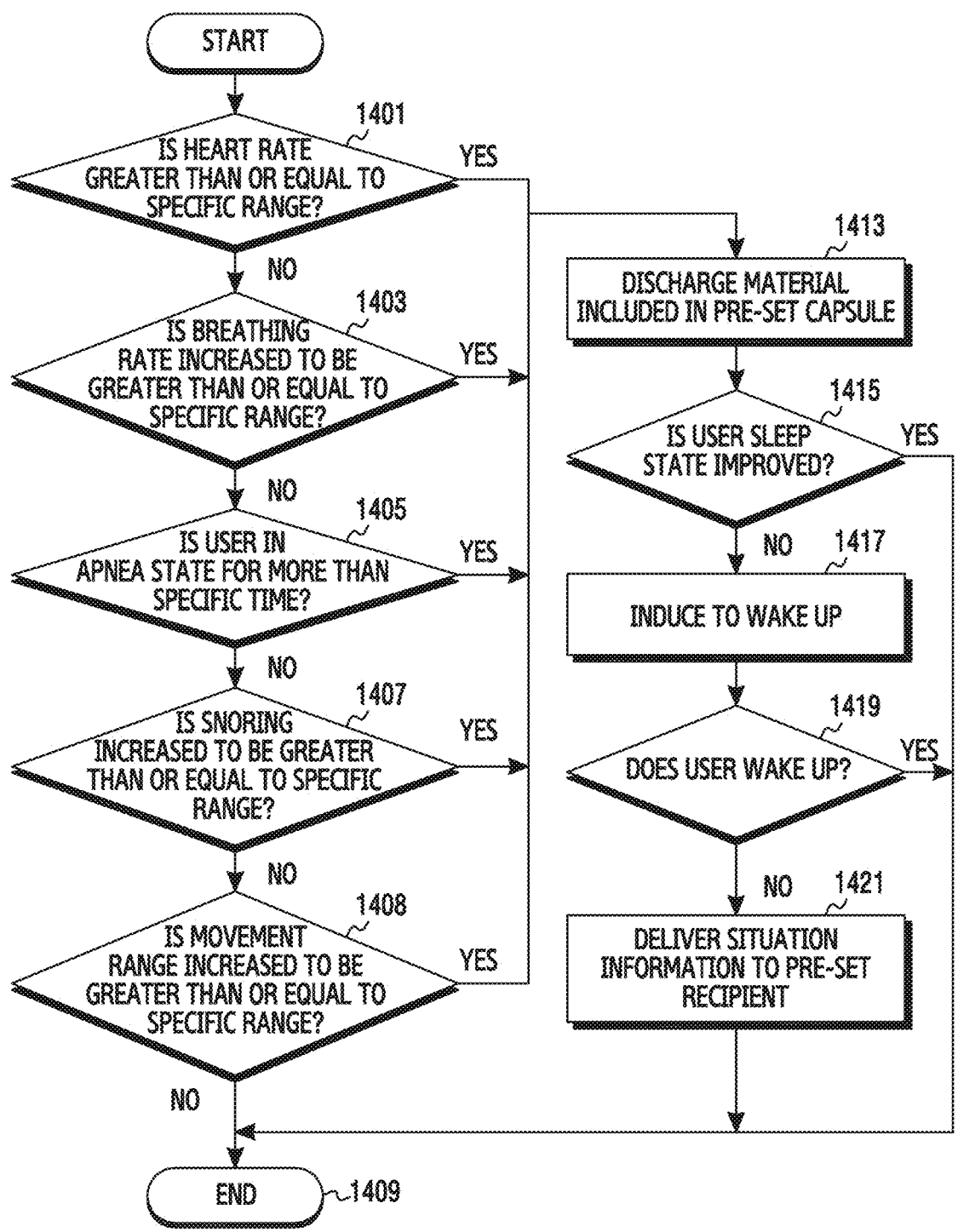

FIGS. 13 and 14 illustrate examples of selecting a capsule and spraying a material included in the capsule on the basis of user's sleep state in an electronic device according to various embodiments of the present disclosure.

Referring to FIG. 13, in operation 1301, the electronic device 200 may determine whether a user enters a deep sleep stage. Whether the user enters the deep sleep stage may be determined on the basis of user's bio information collected from an SD acquisition device, and a detailed determination method is the same as described in FIGS. 9A, 9B, and 10. The deep sleep stage may include NREM sleep stages III and IV. If it is determined that the user enters the deep sleep stage, in operation 1303, the electronic device 200 may determine whether the user maintains a deep sleep during a specific time (e.g., 5 minutes).

The electronic device 200 may determine a user's sleep maintaining state on the basis of user's movement information and bio information, and if it is not determined that the user maintains the deep sleep during 5 minutes, in operation 1307, may determine whether the user enters the deep state again within a specific time (e.g., 5 minutes). When the user enters the deep sleep state again within the specific time, the electronic device 200 repeats operation 1303. If it is determined that the user maintains the deep sleep during the specific time, in operation 1313, the electronic device 200 may select a related capsule according to a previous configuration, and may spray a material included in the capsule. If it is determined that the user fails to maintain the deep sleep during the specific time or the user fails to enter the deep sleep state again within the specific time, in operation 1313, the electronic device 200 may select a capsule related to a previous configuration and may spray a material included in the capsule. The previous configuration may be configured by the user or may be configured through a user's medical record and user customized sleep care service information received by the electronic device 200 via the service server. Further, the previous configuration may be configured on the basis of user's previous sleep pattern data.

If it is determined in operation 1301 that the user fails to enter the deep sleep stage, in operation 1311, the electronic device 200 may determine whether the user stays in an initial sleep stage for more than a specific time (e.g., 10 minutes). If it is determined that the user stays in the initial sleep stage for more than the specific time, the electronic device 300 may perform operation 1313. If it is not determined that the user stays in the initial sleep stage for more than the specific time, the electronic device 200 determines whether the user is currently in a wake-up state or a non-sleep state in operation 1315. The electronic device may end the operation if it is determined that the user is in the wake-up state or the non-sleep state, and may perform operation 1301 if it is not determined that the user is in the wake-up state or the non-sleep state.

In general, since it is difficult to enter the deep sleep stage at once, if the user enters the deep sleep stage within the specific time in operation 1307, the electronic device may determine whether the user maintains the deep sleep during the specific time in operation 1303.

Referring to FIG. 14, in operation 1401, the electronic device 200 may check whether a user's heart rate is greater than or equal to a specific range. If the user's heart rate reaches the specific range, in operation 1413, the electronic device 200 may select a pre-set capsule and spray a material included in the capsule. The electronic device 200 may deliver situation information to a pre-set recipient. For example, current situation information may be transmitted to a terminal carried by a family member of the user or to a hospital system.

If the user's heart rate does not reach the specific range, in operation 1403, the electronic device 200 may determine whether a user's breathing rate is increased to be greater than or equal to a specific range. If the user's breathing rate is increased to be greater than or equal to the specific range, the electronic device 200 may perform operation 1413. If it is determined that the user's breathing rate is not increased to be greater than or equal to the specific range, in operation 1405, the electronic device 200 may determine whether the user is in an apnea state for more than a specific time. If it is determined that the user is in the apnea state for more than the specific time, the electronic device 200 may perform operation 1413.

If it is determined that the user is not in the apnea state, in operation 1407, the electronic device 200 may determine whether user's snoring is increased to be greater than or equal to a specific range. If it is determined that the user's snoring is increased to be greater than or equal to the specific range, in operation 1413, the electronic device 200 may select a pre-set capsule and spray a material included in the capsule.

If it is determined that the user's snoring is not increased to be greater than or equal to the specific range, in operation 1408, the electronic device 200 may determine whether a user's movement range is increased to be greater than or equal to a specific range. If it is determined that the user's movement is increased to be greater than or equal to the specific range, in operation 1413, the electronic device 200 may select a pre-set capsule and spray a material included in the capsule.

In operation 1415, the electronic device 200 may determine whether a user's sleep state is improved after the spraying of the capsule. Whether the user's sleep state is improved may be determined by checking the user's heart rate, breathing rate, apnea state, snoring, and movement range. If the user's heart rate, breathing rate, apnea state, user's heart rate, breathing rate, or the like is decreased to be less than or equal to a specific range, it means that discharging of the capsule is effective, and thus the electronic device may end the operation. Even if there is no change in the breathing rate and the pulse rate even after the discharging of the capsule, the electronic device may determine that the capsule is not effective, determine this as an emergency situation, and artificially wake the user up.

The electronic device 200 may check whether the user's heart rate, breathing rate, apnea state, snoring state, and movement range are decreased to be less than or equal to a specific range, and if it is not determined that those values are decreased to be less than or equal to the specific range, in operation 1417, may enter a wake-up inducing stage to induce the user to wake up. The electronic device 200 may control a sound device, a lighting device, a conditioning device, or the like in order to wake the user up.

In operation 1419, the electronic device 200 determines whether the user wakes up, and if it is determined that the user wakes up, ends the operation. If it is determined in operation 1419 that the user does not wake up, the electronic device 200 may deliver situation information to a pre-set recipient in operation 1421. For example, the electronic device may transmit information regarding the user's heart rate, breathing rate, apnea state, snoring state, and movement range. The pre-set recipient may be, for example, a nurse, a family member, or the like.

Figure 15:
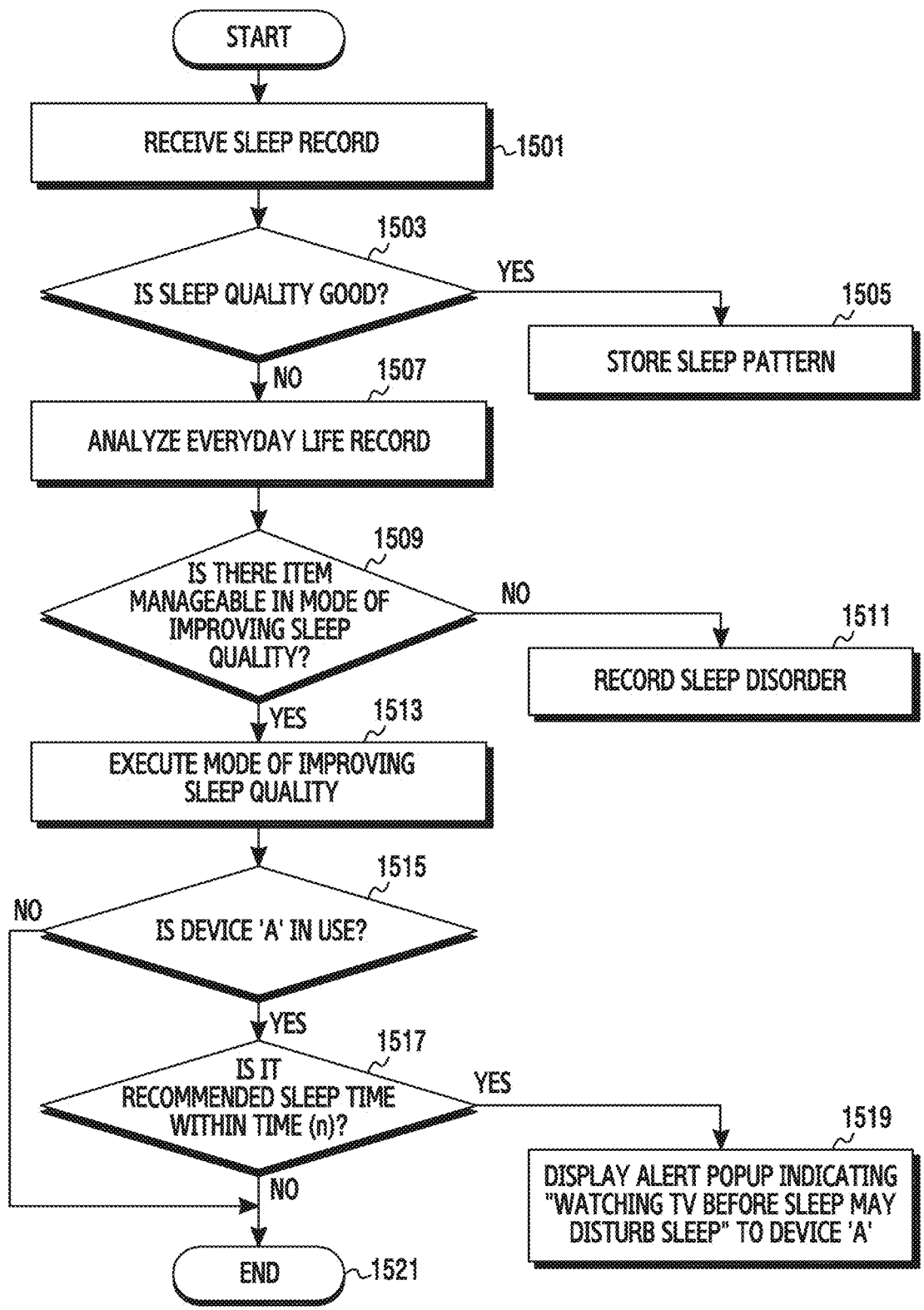
FIG. 15 illustrates an example of receiving, from a sleep management server, sleep record data generated in an electronic device and processing the data according to an embodiment of the present disclosure.

FIG. 15 illustrates an example of receiving, from a sleep management server, sleep record data generated in an electronic device and processing the data according to various embodiments of the present disclosure.

Referring to FIG. 15, the electronic device 200 may collect user's state information and bio information via an SD acquisition device while a user is asleep, and may generate user's sleep record data. The electronic device 200 may transmit the user's sleep record data to a different device, for example, a sleep management server.

In operation 1501, the sleep management server may receive the user's sleep record data. In operation 1503, the sleep management server may analyze the user's sleep record data to determine whether sleep quality is good. If it is determined that the user's sleep quality is good, in operation 1505, the sleep management server may store the sleep record data as a sleep pattern. If it is determined that the sleep quality is not good, in operation 1507, the sleep management server may analyze a user's everyday life record. The user's everyday life record may be acquired via the electronic device 200 or a service server (the service server 400 of FIG. 1). In operation 1509, the sleep management server may determine whether there is an item that can be managed in a mode of improving the user's sleep quality. If there is an item that can be managed to improve the sleep quality, in operation 1513, the sleep management server may execute the mode of improving the sleep quality. If it is determined that there is no item that can be managed in the mode of improving the sleep quality, in operation 1511, the sleep management server may store this as a sleep disorder record. In operation 1515, the sleep management server may check whether the user is using a specific device. If it is determined that the user is using the specific device, the sleep management server checks a user's recommended sleep time, and in operation 1517, may determine whether the recommended sleep time arrives within a specific time. In operation 1519, the sleep management server may control the specific device such that a pre-set notification is displayed to a display unit of the specific device in a popup manner or such that an alert sound is generated.

Figure 16:
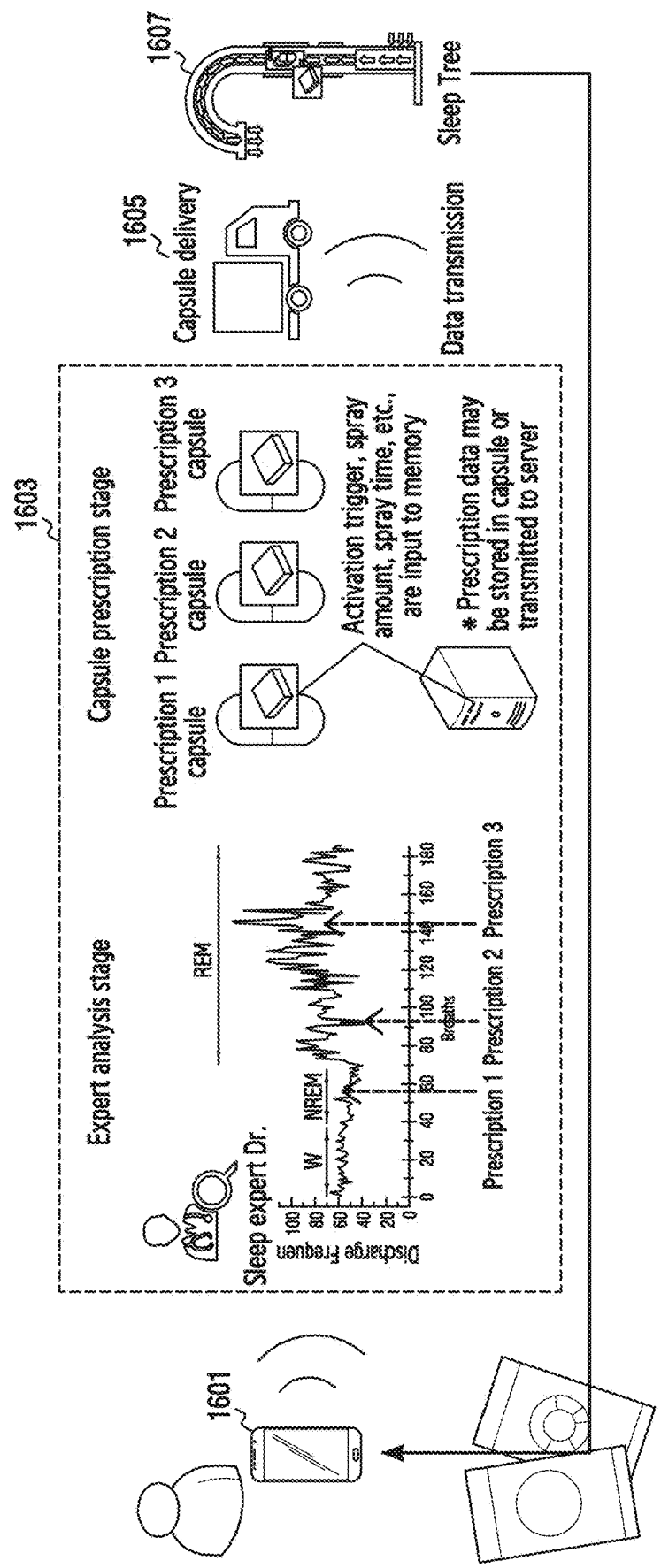
FIG. 16 illustrates an example of analyzing a sleep pattern to prescribe a capsule according to an embodiment of the present disclosure.

FIG. 16 illustrates an example of analyzing a sleep pattern to prescribe a capsule according to an embodiment of the present disclosure.

Referring to FIG. 16, sleep record data generated in an electronic device may be transmitted to a user terminal 1601, and may be transmitted again to a hospital and a sleep management service server 1603. According to a hospital and sleep management service provider, a user's doctor or a designated manager may analyze user's sleep record data and prescribe to improve the user's state. A capsule including a material required for the user may be generated according to the prescription of the doctor or the designated manager. Prescription details of the doctor may be stored in a memory included in the capsule. For example, a trigger condition for selecting the capsule and a spray amount, spray time, or the like of the material included in the capsule may be stored in the memory. Alternatively, information for controlling the capsule may be transmitted to the hospital server 1603 according to the detailed prescription of the doctor. The capsule generated according to the prescription may be delivered to the user via a delivery company 1605, and the user may place the delivered capsule to an electronic device 1607 to have a sleep.

Figure 17:
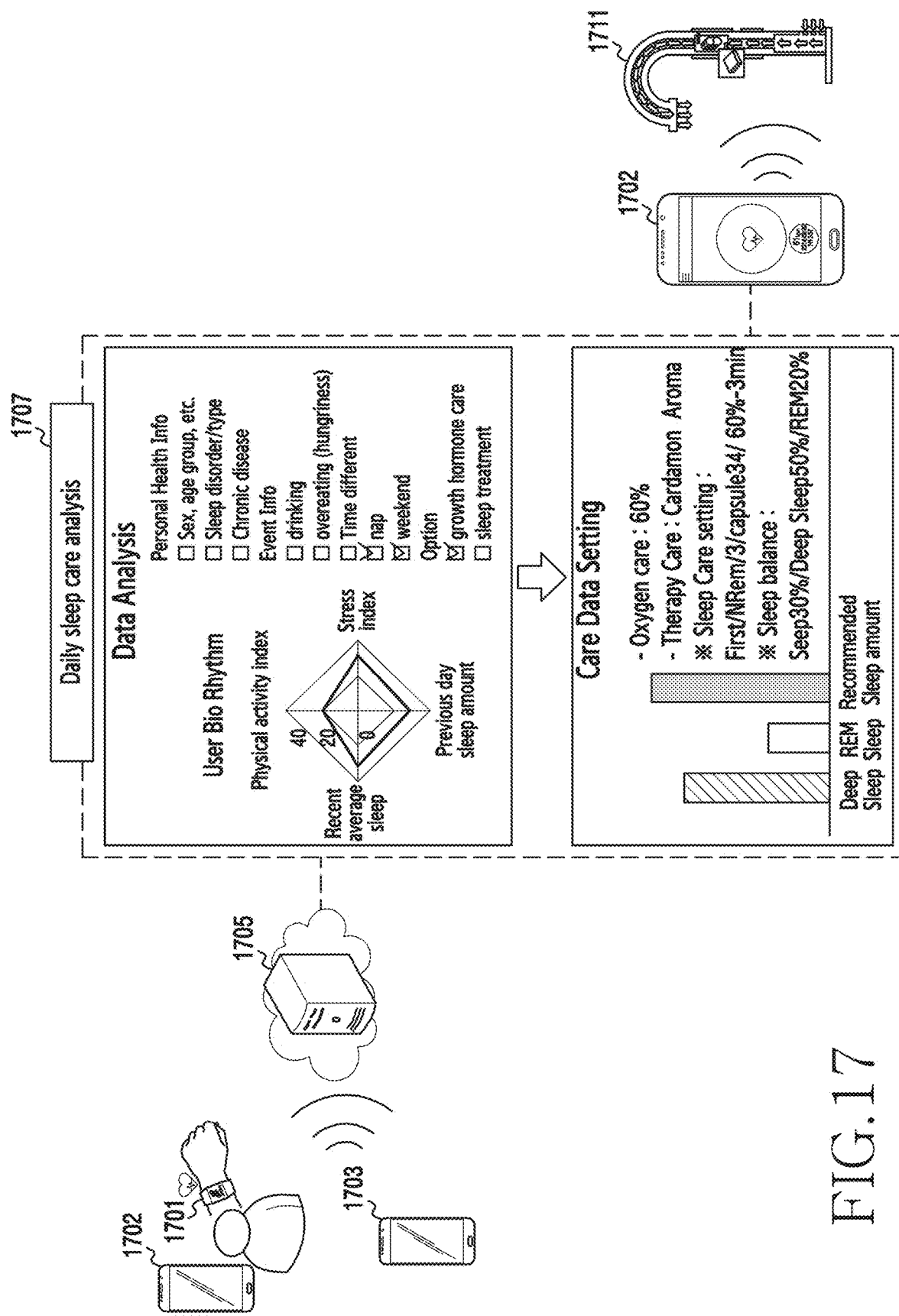
FIG. 17 illustrates an example of providing a sleep care service to a user by an electronic device on the basis of user's activity information and biorhythm information collected during a specific duration according to an embodiment of the present disclosure.

FIG. 17 illustrates an example of providing a sleep care service to a user by an electronic device on the basis of user's activity information and biorhythm information collected during a specific duration according to an embodiment of the present disclosure.

Referring to FIG. 17, the user's activity data may be collected and transmitted to a server 1705 via a wearable device 1701 worn by a user or a user terminal. The wearable device 1701 may transmit the user's activity data and bio information to the server 1705 via a user terminal 1702. The user's activity data may be collected, for example, when the user exercises or walks in a state of wearing the wearable device 1701. Further, the wearable device 1701 may transmit the user's bio information (a pulse rate, a heart rate) to the server 1705 via the user terminal. Alternatively, the wearable device may transmit the user's bio information and exercise related information directly to the server 1705.

An SD acquisition device 1703 may sense the user related information while the user is asleep. The information sensed by the SD acquisition device 1703 is the same as described with reference to FIG. 7. The SD acquisition device 1703 may transmit the sensed user information to the server 1705. The server 1705 may analyze data received from the wearable device 1701, the user terminal 1702, and the SD acquisition device 1703 to generate the user's biorhythm information. The user's biorhythm information may include, for example, fatigability, hungriness, a day activity index, a stress index, a physical activity index, a recent average sleep amount, and a previous day sleep amount. The server 1705 may provide a sleep care service to the user on the basis of the biorhythm information. For example, the server 1705 may analyze the user's biorhythm information so that the electronic device can spray a cardamom aroma material with a concentration of 60%. Further, the server 1705 may analyze the biorhythm information to perform a user's sleep care configuration 1707. For example, the server 1705 may set an electronic device 1711 to spray a material included in a capsule #34 with a concentration of 60% for 3 minutes in a user's NREM sleep stage I. For another example, the server 1705 may set a user's sleep state to a sleep 30%, a deep sleep 50%, and an REM sleep 20%.

Data for configuring the electronic device 1711 may be generated in the server 1705 and may be transmitted to the electronic device 1711 via the user terminal 1702. Alternatively, the data for configuring the electronic device 1711 may be directly transmitted from the server 1705 to the electronic device 1711.

The electronic device 1711 may select a capsule and determine a spray amount and spray time of the capsule on the basis of environment information. The environment information may include an indoor/outdoor temperature, humidity, a fine dust amount, a snowfall amount, and a rainfall amount. The electronic device 1711 may receive the environment information via the user terminal 1702 or the server 1705.

Figure 18:
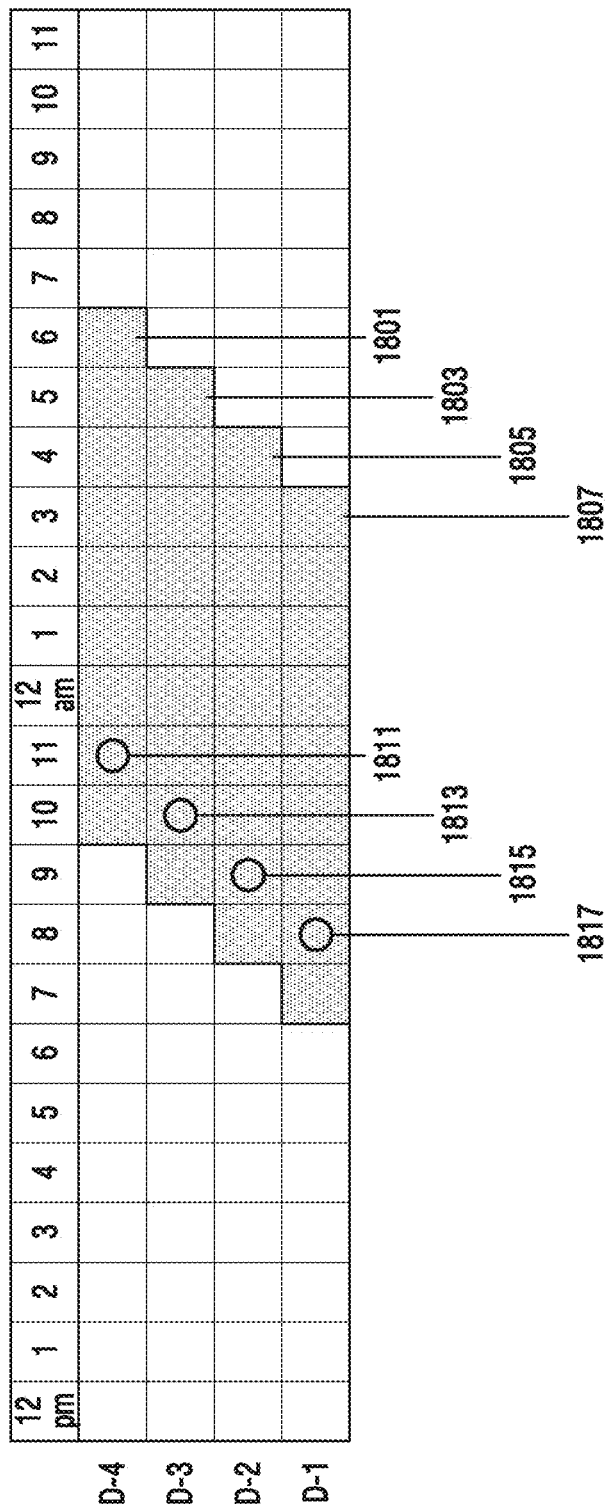
FIG. 18 illustrates an example of an electronic device operating in a time difference adjustment mode according to an embodiment of the present disclosure.

FIG. 18 illustrates an example of an electronic device operating in a time difference adjustment mode according to an embodiment of the present disclosure.

Referring to FIG. 18, in order for the electronic device to operate in the time difference adaptation mode, the electronic device may operate in the time difference adaptation mode on the basis of user's schedule information received from a service server. Alternatively, the electronic device may operate in the time difference adaptation mode by a user's configuration. When the electronic device operates in the time difference adaptation mode, the electronic device may configure a user's bed time and wake-up time by advancing the times by one hour every day. For example, if the user is scheduled to travel to a place having a time difference of 4 hours, the electronic device may be configured such that the user goes to bed 10 o'clock and to wake up 6 o'clock in D-4 (see 1801), and a melatonin material contained in the capsule is sprayed at 11 o'clock (see 1811). The electronic device may analyze the user's bed time and wake-up time for a scheduled duration of the user and determine a regular bed time and wake-up time.

The electronic device may be configured such that the user goes to bed at 9 o'clock and wakes up at 5 o'clock in D-3 (see 1803), and melatonin contained in a capsule is sprayed at 10 o'clock (see 1813). The electronic device may be configured such that the user goes to bed at 8 o'clock and wakes up at 4 o'clock in D-2 (see 1805), and melatonin contained in a capsule is sprayed at 9 o'clock (see 1813). The electronic device may be configured such that the user goes to bed at 7 o'clock and wakes up at 3 o'clock in D-1 (see 1807), and melatonin contained in a capsule is sprayed at 10 o'clock (see 1817). Further, according to implementations, the user may configure a bedtime and wake-up time to be advanced every day. For example, if the user configures the bedtime and the wake-up time to 2 hours, the electronic device may advance the bedtime and the wake-up time by 2 hours every day.

If it is a bedtime, the electronic device may select a capsule containing a material for inducing the user to sleep, and may spray the material included in the capsule. If it is a wake-up time, in order to induce the user to wake up, the electronic device may control a lighting device to light a room, or control a conditioning device to drive a conditioner, or may control a sound device to reproduce music. Since an example of operating the electronic device at the bedtime and the wake-up time is the same as described in FIG. 10, detailed descriptions thereof will be omitted.

The electronic device may determine a date for adjusting the user's bedtime and wake-up time on the basis of user's travel schedule information received from the service server. The travel schedule information may include a user's travel region and travel period. The electronic device may calculate a time difference from travel region information included in the travel schedule information, and may determine a date of starting to advance the bedtime and the wake-up time. For example, if the user has a plan to travel to a region having a time difference of 5 hours, the electronic device may adjust the bedtime and the wake-up time starting from 5 days before the travel. If the user has a plan to travel to a region having a time difference of 7 hours, the electronic device may adjust the bedtime and the wake-up time starting from 7 days before while traveling.

According to the sleep management service provided by the electronic device, user's sleep management data may be shared via the service server, and the sleep management data may be offered to the user from the service server during the travel.

Each of the aforementioned constitutional elements of the electronic device 200 may consist of one or more components, and names thereof may vary depending on a type of electronic device. The electronic device according to various embodiments may include at least one of the aforementioned constitutional elements. Some of the constitutional elements may be omitted, or additional other constitutional elements may be further included. In addition, some of the constitutional elements of the electronic device according to various embodiments may be combined and constructed as one entity, so as to equally perform functions of corresponding constitutional elements before combination.

A term "module" used in the present document may imply a unit including, for example, one of hardware, software, and firmware or a combination of two or more of them. The "module" may be interchangeably used with a term such as a unit, a logic, a logical block, a component, a circuit, and the like. The "module" may be a minimum unit of an integrally constituted component or may be a part thereof.

The "module" may be a minimum unit for performing one or more functions or may be a part thereof. The "module" may be mechanically or electrically implemented. For example, the "module" may include at least one of an application-specific IC (ASIC) chip, a field-programmable gate arrays (FPGAs), and a programmable-logic device, which are known or will be developed and which perform certain operations.

According to various embodiments, at least some parts of a device (e.g., modules or functions thereof) or method (e.g., operations) may be implemented with an instruction stored in a computer-readable storage media for example. If the instruction is executed by one or more processors (e.g., the processor 111), the one or more processors may perform a function corresponding to the instruction. The computer-readable storage media may be, for example, the memory 113.

The computer readable recording medium may be a hardware device configured particularly to store and perform a program instruction (e.g., program module), for example, a hard disk, a magnetic medium such as a floppy disc and a magnetic tape, an optical storage medium such as a compact disc-ROM (CD-ROM) or a digital versatile disc (DVD), a magnetic-optic medium such as a floptical medium, a ROM, a RAM, a flash memory, and the like. An example of the program instruction includes not only a machine language created by a compiler but also a high-level language executable by a computer by using an interpreter or the like. The aforementioned hardware device may be configured to operate as one or more software modules to perform the operation of various embodiments of the present disclosure, and the other way around is also possible.

The module or programming module according to various embodiments may further include at least one or more constitutional elements among the aforementioned constitutional elements, or may omit some of them, or may further include additional other constitutional elements. Operations performed by a module, programming module, or other constitutional elements may be executed in a sequential, parallel, repetitive, or heuristic manner. In addition, some of the operations may be executed in a different order or may be omitted, or other operations may be added.

According to various embodiments, in a storage medium for storing instructions, when the instructions are executed by at least one processor, the at least one processor may be allowed to perform at least one operation including acquiring an image, and outputting a message generated on the basis of additional information and an image analysis result obtained by analyzing the acquired image.

According to various embodiments, an electronic device may receive user's state information and bio information via a communication unit, and spray a material capable of inducing a sleep and maintaining a deep sleep on the basis of the user's state information and bio information, thereby allowing a user to have the deep sleep.

While the present disclosure has been shown and described with reference to various embodiments thereof, it will be understood by those skilled in the art that various changes in form and details may be made therein without departing from the spirit and scope of the present disclosure as defined by the appended claims and their equivalents.

The invention claimed is:

1. An electronic device comprising:
   a first flow passage tube formed in the electronic device;
   a second flow passage tube formed in the electronic device, wherein a flow passage tube comprises the first flow passage tube and the second flow passage tube;
   a capsule container configured to contain a plurality of capsules and disposed between the first flow passage tube and the second flow passage tube, wherein the first flow passage tube and the second flow passage tube are connected through the capsule container;
   an outlet disposed at an end of the first flow passage tube;
   a conditioner disposed at an end of the second flow passage tube and configured to allow air to enter the electronic device;
   a transceiver configured to transmit data to an external device or to receive data from the external device; and
   at least one processor operatively coupled to the capsule container, the conditioner, and the transceiver, wherein the at least one processor is configured to:
      receive user state information and biometric information from the external device via the transceiver,
      select at least one of the plurality of capsules in the capsule container based on the received user state information and the received biometric information,
      determine a spray amount of a material contained in the selected at least one capsule,
      control the capsule container so that the determined spray amount of the material contained in the selected at least one capsule is sprayed into the first flow passage tube, and
      control the conditioner to spray the material within the first flow passage tube out of the electronic device through the outlet.

2. The electronic device of claim 1, wherein the at least one processor is further configured to:
   determine a spray time of the material within the flow passage tube based on the received user state information and the received biometric information, and
   control the conditioner to spray the material within the flow passage tube in the determined spray time.

3. The electronic device of claim 1, wherein the biometric information contains at least one of a heartbeat, a pulsation, or a breath.

4. The electronic device of claim 3, wherein the at least one processor is further configured to:
   determine a sleep state period based on the received user state information and the received biometric information,
   select the at least one of the plurality of capsules based on the determined sleep state period, and
   determine the spray amount and a spray time of the material contained in the selected at least one capsule based on the determined sleep state period.

5. The electronic device of claim 3, wherein the at least one processor is further configured to:
   determine a user's sleep state based on the received user state information and the received biometric information,
   select the at least one of the plurality of capsules based on the user's sleep state, and
   determine the spray amount and a spray time of the selected at least one capsule based on the user's sleep state.

6. The electronic device of claim 1,
   wherein each of the plurality of the capsules includes at least one memory, and
   wherein the at least one processor is further configured to:
      select the at least one of the plurality of capsules based on a set value stored in the at least one memory, and
      determine the spray amount and a spray time of the selected at least one capsule based on the set value stored in the at least one memory.

7. The electronic device of claim 1, wherein the at least one processor is further configured to:
   select the at least one capsule based on weather information, and
   determine the spray amount and a spray time of the selected at least one capsule based on the weather information.

8. The electronic device of claim 1, wherein the at least one processor is further configured to:
   determine a user's customized sleep care information and a user's preferred sleep care information via the transceiver,
   select the at least one capsule based on the user's customized and preferred sleep care information, and
   determine the spray amount and a spray time of the selected at least one capsule based on the user's customized and preferred sleep care information.

9. The electronic device of claim 1, wherein the at least one processor is further configured to:
   receive service information via the transceiver,
   select the at least one capsule based on the received service information, and
   determine the spray amount and a spray time of the selected at least one capsule based on the service information.

10. The electronic device of claim 1, wherein the at least one processor is further configured to:
    receive a user's medical record via the transceiver,
    select the at least one capsule based on the user's medical record, and
    determine the spray amount and a spray time of the selected at least one capsule based on the user's medical record.

11. The electronic device of claim 1, wherein the at least one processor is further configured to:
    receive a wearable device usage history of a user via the transceiver,
    select the at least one capsule based on the wearable device usage history of the user, and
    determine the spray amount and a spray time of the selected at least one capsule of the plurality of capsules based on the wearable device usage history.

12. The electronic device of claim 1, wherein the at least one processor is further configured to:
    receive user history information stored in a user terminal via the transceiver,
    select the at least one capsule based on the user history information, and
    determine the spray amount and a spray time of the selected at least one capsule of the plurality of capsules based on the user history information.

13. The electronic device of claim 12, wherein the user history information contains at least one of a stress index of a user, a sleep amount of a previous data, a sleep amount for a specific duration, a sleep level, food intake information, a physical activity amount, time difference information, or electronic device usage information.

14. The electronic device of claim 1, wherein the at least one processor is further configured to:
    receive data related to a life pattern of a user via the transceiver,
    select the at least one capsule based on the data related to the life pattern of the user, and
    determine the spray amount and a spray time of the selected at least one capsule based on the life pattern of the user.

15. The electronic device of claim 1, further comprising at least one of an infrared image camera, a microphone, an air quality sensor, an illumination sensor, an oxygen generator, an anion generator, a virus doctor, a lighting device, or an audio device.

16. The electronic device of claim 1,
    wherein the conditioner includes at least one of an oxygen generating device, an anion generating device, a bacteriostatic device, or an air cleaning device.

17. The electronic device of claim 1,
    wherein the first flow passage tube including a bent portion, and
    wherein the second flow passage tube extends substantially straightly from the conditioner to the capsule container.

18. The electronic device of claim 1,
    wherein the capsule container includes a plurality of valves,
    wherein each of the plurality of valves is configured to spray the material included in each of the plurality of capsules to the first flow passage tube, and
    wherein the at least one processor is further configured to:
       control the each of the plurality of valves to spray the material included in the selected at least one capsule based on the determined spray amount.

19. The electronic device of claim 1, wherein the conditioner includes a fan or a blower.

20. A method of controlling an electronic device comprising a flow passage tube and a capsule container penetrated by the flow passage tube and disposed between a first end of the flow passage tube and a second end of the flow passage tube, the method comprising:
    receiving user state information and biometric information from an external device via a transceiver;
    selecting at least one capsule in the capsule container based on the received user state information and the received biometric information;
    determining a spray amount of a material contained in the selected at least one capsule;
    spraying the determined spray amount of the material into the flow passage tube; and
    spraying, by using a conditioner disposed at the first end, the material within the flow passage tube to outside of the electronic device through an outlet, wherein the outlet is disposed at the second end.

* * * * *